(12) United States Patent
Jin et al.

(10) Patent No.: US 11,319,392 B2
(45) Date of Patent: May 3, 2022

(54) COMPOSITIONS AND METHODS TO ANTIBACTERIAL NANOGEL AND HYDROLYTICALLY STABLE ANTIBACTERIAL NANOGEL FOR DENTAL COMPOSITIONS

(71) Applicant: DENTSPLY SIRONA Inc., York, PA (US)

(72) Inventors: Xiaoming Jin, Middletown, DE (US); Christian Scheufler, Engen (DE); Joachim E. Klee, Radolfzell (DE); Hui Lu, Magnolia, DE (US)

(73) Assignee: DENTSPLY SIRONA INC., York, PA (US)

( * ) Notice: Subject to any disclaimer, the term of this patent is extended or adjusted under 35 U.S.C. 154(b) by 204 days.

(21) Appl. No.: 16/555,217

(22) Filed: Aug. 29, 2019

(65) Prior Publication Data

US 2020/0157266 A1   May 21, 2020

Related U.S. Application Data

(60) Provisional application No. 62/769,715, filed on Nov. 20, 2018.

(51) Int. Cl.
| | |
|---|---|
| *C08F 220/60* | (2006.01) |
| *A61K 6/887* | (2020.01) |
| *C08F 293/00* | (2006.01) |
| *C08J 3/075* | (2006.01) |
| *B82Y 30/00* | (2011.01) |

(52) U.S. Cl.
CPC ............ *C08F 220/60* (2013.01); *A61K 6/887* (2020.01); *C08F 293/005* (2013.01); *C08J 3/075* (2013.01); *B82Y 30/00* (2013.01)

(58) Field of Classification Search
CPC ....................................................... A61K 6/887
See application file for complete search history.

(56) References Cited

U.S. PATENT DOCUMENTS

| | | |
|---|---|---|
| 5,494,987 A | 2/1996 | Imazato |
| 6,710,181 B2 | 3/2004 | Kumagai |
| 7,094,845 B2 | 8/2006 | Kumagai |

(Continued)

FOREIGN PATENT DOCUMENTS

| | | |
|---|---|---|
| CN | 105199577 A | 12/2015 |
| WO | 2010132270 A1 | 11/2010 |

(Continued)

OTHER PUBLICATIONS

International Search Report; PCT/US2019/048779; Nov. 28, 2019 (completed); dated Dec. 5, 2019.

(Continued)

*Primary Examiner* — Michael F Pepitone
(74) *Attorney, Agent, or Firm* — Dentsply Sirona Inc.

(57) ABSTRACT

Described herein are a polymerizable antibacterial nanogel and hydrolytically stable antibacterial nanogel composition and methods of preparing such compositions, use of polymerizable antibacterial nanogels and hydrolytically stable antibacterial nanogels as additives to a dental product, such as a resin monomer, a cement, an adhesive and composite formulations. Methods and compositions for forming hydrolytically stable antibacterial monomers are also described.

28 Claims, 6 Drawing Sheets

(56) References Cited

U.S. PATENT DOCUMENTS

| | | |
|---|---|---|
| 7,553,881 B2 | 6/2009 | Salz |
| 8,747,831 B2 | 6/2014 | Jin |
| 9,138,383 B1 | 9/2015 | Stansbury |
| 9,845,415 B2 | 12/2017 | Stansbury |
| 10,894,885 B2 * | 1/2021 | Naier .................. C08F 26/06 |
| 2010/0256242 A1 | 10/2010 | Antonucci |
| 2011/0245127 A1* | 10/2011 | Suzuki ................. C11D 1/008 |
| | | 510/163 |
| 2015/0037535 A1* | 2/2015 | Akimoto .............. C09C 1/3072 |
| | | 428/141 |
| 2015/0240103 A1* | 8/2015 | Farnham ............... C09D 11/52 |
| | | 427/98.4 |
| 2017/0057933 A1* | 3/2017 | Jin ....................... C07F 9/6521 |
| 2017/0143594 A1* | 5/2017 | Lu ......................... A61K 6/30 |
| 2017/0280725 A1* | 10/2017 | Jin ....................... A01N 57/34 |

FOREIGN PATENT DOCUMENTS

| | | | |
|---|---|---|---|
| WO | 2012177960 A1 | 12/2012 | |
| WO | 2015066254 A1 | 5/2015 | |
| WO | 2016182444 A1 | 11/2016 | |
| WO | WO-2017144180 A1 * | 8/2017 | .............. C09G 3/00 |

OTHER PUBLICATIONS

Written Opinion of the International Searching Authority; PCT/US2019/048779; Nov. 28, 2019 (completed); Dec. 5, 2019.
Stansbury et al, "Improved Dental Adhesive Formulations Based on Reactive Nanogel Additives"; Journal of Dental Research, 2012; pp. 179-184, vol. 91(2).

* cited by examiner

Table I: Antibacterial Activity of Antibacterial Composite (ZL1-99/ZL1-90) against *S. aureus*

| Test Microorganism | Contact Time | Carrier Type | CFU/Carrier | Percent Reduction Compared to Control at Contact Time | Log10 Reduction Compared to Control at Contact Time |
|---|---|---|---|---|---|
| S. aureus 6528 | Time Zero | ATL Control | 5.20E+5 | N/A | |
| | | ZL1-99 | 4.85E+2 | 99.97% | 3.54 |
| | | ZL1-90 | <5.00E+00 | >99.9997% | >5.53 |

- The limit of detection for this assay is 5CFU/Carrier. Value below the limit of detection are noted as <5.00E+00 CFU in the table

FIG. 2

Table II: Antibacterial Activity of Antibacterial Composite (ZL1-125/ZL1-137) against *S. aureus*

| Test Microorganism | Contact Time | Carrier Type | CFU/Carrier | Percent Reduction Compared to Control at Contact Time | Log10 Reduction Compared to Control at Contact Time |
|---|---|---|---|---|---|
| S. aureus 6528 | Time Zero | Control | 7.50E+5 | N/A | |
| | | ATL Control | 4.70E+6 | | |
| | | ZL1-125 | <5.00E+00 | 99.99989% | >5.97 |
| | | ZL1-137 | <5.00E+00 | >99.99989% | >5.97 |

- The limit of detection for this assay is 5CFU/Carrier. Value below the limit of detection are noted as <5.00E+00 CFU in the table

FIG. 3

COMPOSITIONS AND METHODS TO ANTIBACTERIAL NANOGEL AND HYDROLYTICALLY STABLE ANTIBACTERIAL NANOGEL FOR DENTAL COMPOSITIONS

FIELD OF THE DISCLOSURE

The present disclosure relates to a polymerizable antibacterial nanogel and hydrolytically stable antibacterial nanogel composition and methods of preparing such compositions, use of polymerizable antibacterial nanogels and hydrolytically stable antibacterial nanogels as additives to a dental product, such as a resin monomer, a cement, an adhesive and composite formulations. The disclosure also relates to methods and compositions for forming hydrolytically stable antibacterial monomers.

BACKGROUND OF THE DISCLOSURE

Nanogel modified dental material such as adhesive were introduced by Stansbury et al (Journal of Dental Research (2012), 91(2), 179-184) as a solution to control the material's hydrophobic character without changing the basic monomer formulation. Various nanogels were synthesized by Stansbury et al based on monomers such as IBMA/UDMA; HEMA/BisGMA and HEMA/TEGDMA. The more hydrophobic IBMA/UDMA nanogel showed higher bulk mechanical property results, but the best dentin bond strength values, and strength values that improved upon storage were obtained with the amphiphilic nanogel based on BisGMA/HEMA. Control of polymerization shrinkage and stress in nanogel-modified monomer and composite materials were also achieved by use of reactive nanogels.

U.S. Pat. No. 9,138,383 disclosed soluble nanogel polymers produced by polymerization of a monomer mixture comprising a monovinyl monomer, divinyl monomer, a chain transfer agent and an iniferter.

U.S. Pat. No. 9,845,415 disclosed a water dispersible nanogel produced by a process comprising: (i) combining a monomer mixture comprising at least one monovinyl monomer, at least one divinyl monomer, a difunctional chain transfer agent, and an initiator; and (ii) polymerizing said mixture to form the water dispersible nanogel; wherein said at least one monovinyl monomer comprises polyethoxy (10) ethyl methacrylate (E10 HEMA).

Further, in restorative dentistry, extensive attempts have been made to create dental compositions with antibacterial/antimicrobial effects, by incorporation of a variety of antibacterial/antimicrobial agents, such as chlorhexidine, silver ions, zinc ions, and fluoride, etc. Although such low molecular compounds demonstrated certain immediate effectiveness, there are controversial related to their long-term effectiveness, esthetics, potential toxicity, and impact to the mechanical strength of the formulated dental composition due to the leachability. On the other hand, solid antibacterial/antimicrobial agents such as silver nanoparticles and polymeric quantum ammonium salt (QAS) nanoparticles were also developed to address those issues associated with the low molecular weight of antibacterial/antimicrobial agents. There are also issues such as color, optical opacity, and mechanical strength. Recently polymerizable antibacterial/antimicrobial resins were developed but their sub-optimal effectiveness require relatively high loading level, and most of them demonstrated negative impact on mechanical property in the formulated dental compositions, with the increased concentration.

U.S. Publication No. 2010/0256242 disclosed a polymerizable biomedical composition that includes a quaternary ammonium group bonded at its quaternary sites.

U.S. Pat. No. 5,494,987 disclosed antimicrobial polymerizable compositions having an ethylenically unsaturated monomer with antimicrobial activity for dental application composed of quaternary ammonium dodecylpyridinium (MDPB).

U.S. Pat. Nos. 6,710,181 and 7,094,845 disclosed an imidazole-based silane and monocarboxylic acid salt for improving adhesion between resins and metal or glass.

U.S. Pat. No. 7,553,881 disclosed dental compositions based on polymerizable macromers based on quaternary ammonium salts for antimicrobial effect.

U.S. Pat. No. 8,747,831 disclosed dental composition and method of making a polymerizable antibacterial/antimicrobial resin and using such a bioactive resin in formulated dental compositions.

U.S. Publication No. 2017/0143594 disclosed a method and orthodontic cement composition comprising polymerizable antibacterial/microbial monomers, and a high performance orthodontic cement formulated from such novel bioactive resins.

SUMMARY OF THE DISCLOSURE

There is continued interest to develop dental products such as adhesive, composites and cement having antibacterial activity, non-leachability, low dose loading without jeopardizing mechanical integrity for the formulated dental products by introducing polymerizable antibacterial nanogel and hydrolytically stable antibacterial nanogel into the dental product.

The present disclosure provides a polymerizable antibacterial nanogel and hydrolytically stable antibacterial nanogel composition and methods of preparing such compositions, use of polymerizable antibacterial nanogels and hydrolytically stable antibacterial nanogels as additives to a dental product, such as a resin monomer, a cement, an adhesive and composite formulations. The disclosure also relates to methods and compositions for forming hydrolytically stable antibacterial monomers.

In a first aspect of the disclosure, the polymerizable antibacterial nanogel is derived from a monomer mixture comprising:

(a) a polymerizable antibacterial monomer having at least one of imidazolium, pyridinium, ammonium or sulfonium group and at least one ethylenically unsaturated group, (b) at least one polymerizable resin monomer having at least one (meth)acrylate or (meth)acrylamide group, (c) at least one chain transfer agent, and (d) an initiator.

More specifically, the polymerizable antibacterial nanogel disclosed herein is related to methods of deriving such polymerizable antibacterial nanogel that includes polymerizable antibacterial monomer, as shown in a compound of Formula I

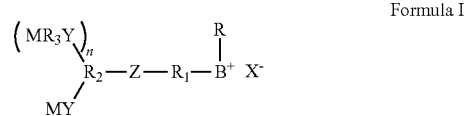

wherein,
M is vinylether, vinylester, vinylamine, allyl, acrylamide, methacrylamide, acrylate, or methacrylate moiety;
Y and Z are an independently a same or different alkylene, oxyalkylene, aminoalkylene or thioalkylene having from 1 to 4 carbons, arylene, carbonate, carboxylate, ester group, amide or a direct bond;
$R_1$ is a divalent hydrocarbon radical having from 2 to 18 carbons;
$R_2$ and $R_3$ are an independently a same or different straight or branched chain alkylene having from 1 to 4 carbons or a direct bond;
B is an imidazolium, pyridinium, ammonium or sulfonium group;
R is a linear or branched alkyl having from 4 to 16 carbon atoms or a direct bond;
X is a counter ion moiety; and
n is an integer of from 0 to 4.

In an embodiments of the polymerizable antibacterial nanogel disclosed herein, the polymerizable antibacterial monomer comprises a compound of Formula II

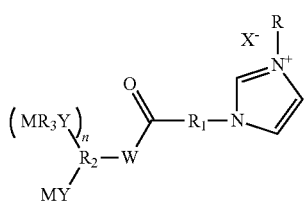

Formula II wherein,
M is vinylether, vinylester, vinylamine, allyl, acrylamide, methacrylamide, acrylate, or methacrylate moiety;
Y is an alkylene, oxyalkylene or thioalkylene having from 1 to 4 carbons, carbonate, carboxylate, ester group, or direct bond;
W is O, $NR_4$ or a direct bond;
$R_1$ is a divalent hydrocarbon radical having from 2 to 18 carbons;
$R_2$ and $R_3$ are an independently a same or different straight or branched chain alkylene having from 1 to 4 carbons;
$R_4$ is an alkyl having from 1 to 4 carbons or $R_2M$;
R is a linear or branched alkyl having from 4 to 16 carbon atoms;
X is a counter ion moiety; and
n is an integer of from 0 to 1.

In one particular embodiment, the polymerizable antibacterial monomer comprises a compound of Formula III

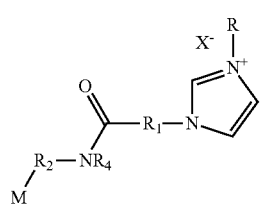

Formula III wherein,
M is allyl, acrylamide, or methacrylamide moiety;
$R_1$ is a divalent hydrocarbon radical having from 2 to 18 carbons;

$R_2$ is an independently a same or different straight or branched chain alkylene having from 1 to 4 carbons;
$R_4$ is an alkyl having from 1 to 4 carbons or $R_2M$;
R is a linear or branched alkyl having from 4 to 16 carbon atoms; and
X is a counter ion moiety.

In another embodiment of the polymerizable antibacterial nanogel disclosed herein, the polymerizable resin monomer having at least one (meth)acrylate or methacrylamide group is selected from the group consisting of mono-, di-, tri- or tetra functional monomer.

In yet another embodiment of the polymerizable antibacterial nanogel disclosed herein, the at least one chain transfer agents is 1-dodecanethiol.

In yet further embodiments of the polymerizable antibacterial nanogel disclosed herein, the initiator is azobisisobutyronitrile.

In a second aspect of the disclosure, a method of forming a hydrolytically stable, water soluble polymerizable antibacterial monomer containing asymmetric polyacrylamides is provided.

The method includes the steps of:
(a) reacting an asymmetric polyacrylamide of formula

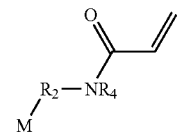

in the presence of a Michael donor under conditions selected to yield mono-substituted asymmetric polyacrylamide of formula

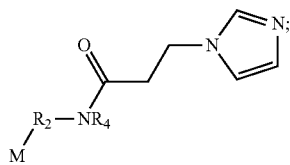

wherein the Michael donor is imidazole;
(b) converting the imidazole of mono-substituted asymmetric polyacrylamide monomer to an imidazolium by reacting mono-substituted asymmetric polyacrylamide monomer with RX to yield hydrolytically stable, water soluble polymerizable antibacterial monomer containing asymmetric polyacrylamides of Formula III

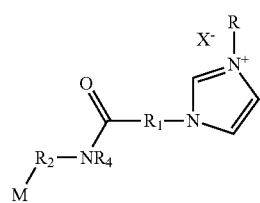

wherein
M is allyl, acrylamide, or methacrylamide moiety;
$R_1$ is a divalent hydrocarbon radical having from 2 to 18 carbons;

$R_2$ is an independently a same or different straight or branched chain alkylene having from 1 to 4 carbons;

$R_4$ is an alkyl having from 1 to 4 carbons or $R_2M$.

R is a linear or branched alkyl having from 4 to 16 carbon atoms; and

X is a counter ion moiety.

In a third aspect of the disclosure, a method of preparing a polymerizable antibacterial nanogel is provided. The method includes the steps of:

(a) combining a polymerizable antibacterial monomer having at least one of imidazolium, pyridinium, ammonium or sulfonium group and at least one (meth)acrylate group, at least one polymerizable resin monomer having at least one (meth)acrylate or (meth)acrylamide group, at least one chain transfer agent, and an initiator in presence of a solvent in a microwave reactor, (b) initiating a polymerization reaction, and (c) recovering the polymerizable antibacterial nanogel from the solvent after polymerization.

The solvent useful in the method disclosed herein plays an important role in the nanogel formation because no macrogel was formed from nanogel when methyl ethyl ketone was used as the solvent. The formation of such a macrogel is critical for the redispersability of the nanogel in resin matrix. Different results were achieved when toluene was used as the solvent.

Formulated dental compositions, including adhesives, cements and composites, derived from the nanogel described herein demonstrated improved antibacterial effectiveness and mechanical properties, such as improved bonding strength and significantly reduced polymerization shrinkage and stress.

BRIEF DESCRIPTION OF THE DRAWINGS

FIG. 2 depicts a Table I demonstrating antibacterial activity of a composite according to the present disclosure against *S. aureus*.

FIG. 3 depicts a Table II demonstrating antibacterial activity of a composite according to the present disclosure against *S. aureus*.

DETAILED DESCRIPTION OF THE DISCLOSURE

Figure 1:
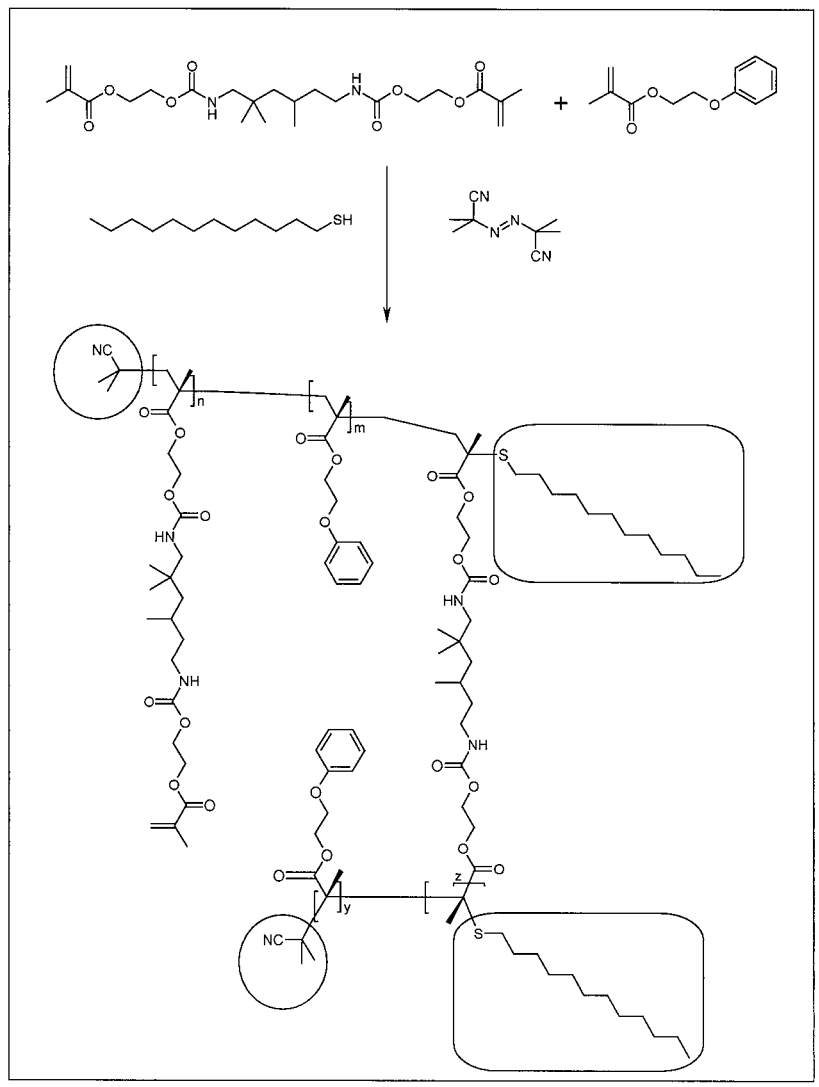
FIG. 1 depicts a polymerization and structure of di(methacryloxyethyl)trimethyl-1,6-hexaethylenediurethane (UDMA)/2-phenoxyethyl (meth)acrylate (POEMA), a conventional polymerizable nanogel via thermal free radical polymerization with azobisisobutyronitrile (AIBN) and mediated with 1-dodecanethiol (DDT) as chain transfer agent.

The above-mentioned aspects, as well as other aspects, features, and advantages of the present disclosure are described below in connection with various embodiments, with reference made to the accompanying figures.

Some of the terms used in the present disclosure are defined below: The term "alkyl", unless otherwise specified, refers to a monoradical branched or unbranched saturated hydrocarbon chain having from 1 to 18 carbon atoms. This term can be exemplified by groups such as methyl, ethyl, n-propyl, iso-propyl, n-butyl, iso-butyl, sec-butyl, t-butyl, n-pentyl, isopentyl, neopentyl, n-hexyl, n-decyl, dodecyl, tetradecyl, and the like. Alkyl groups may be substituted further with one or more substituents selected from alkenyl, alkoxy, and hydroxyl.

The term "alkylene", unless otherwise specified refers to a linear saturated divalent hydrocarbon radical of one to four carbon atoms or a branched saturated divalent hydrocarbon radical of three to four carbon atoms, e.g., methylene, ethylene, 2,2-dimethylethylene, propylene, 2-methylpropylene, butylene and the like, preferably methylene, ethylene, or propylene.

The term "oxyalkylene" refers to an alkylene-O-group wherein alkylene is as previously described.

The term "aminoalkylene" refer to an alkylene radicals substituted with amino radicals. More preferred are "lower aminoalkylene" radicals. Examples of such radicals include aminomethylene, aminoethylene, and the like.

The term "thioalkylene" refers to an alkylene radical substituted by —S—. Examples of such radical include methylenethio, ethylenethio, n-propylenethio, i-propylenethio, n-butylenethio, i-butylenethio, s-butylenethio, and t-butylenethio.

The term "arylene" is the divalent moiety of "aryl". The term "aryl" refers to C5-C10-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those "aryl" groups having heteroatoms in the ring structure may also be referred to as "aryl" or "heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1, 5,2-dithiazinyl, dihydrofuro[2,3b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2, 4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl.

The term "(meth)acrylate" in the context of the present disclosure is meant to refer to the acrylate as well as to the corresponding methacrylate.

The term "(meth)acrylamide" in the context of the present disclosure is meant to include acrylamide and methacrylamide.

The term "divalent hydrocarbon radical" refers to divalent hydrocarbon radicals having 2 to 18 carbon atoms include alkylene radicals such as ethylene, methylmethylene, propylene, butylene, pentylene, hexylene and octadecylene; alkylene radicals such as vinylene, allylene and butadienylene; cycloalkylene radicals such as cyclobutylene, cyclopentylene and cyclohexylene; cycloalkenylene radicals such as cyclopentenylene and cyclohexenylene; arylene radicals such as phenylene and xenylene; aralkylene radicals as benzylene; and alkarylene radicals such as tolylene.

The term "counter ion moiety" refers to an ion having a charge opposite to that of the substance with which it is associated. Examples of counter ion moiety include but are not limited to chloride, bromide, iodide, hydroxide, carboxylate, amino acid, phosphate, sulfate or nitrate.

The term "nanogel" refers to soluble or dispersible highly branched polymeric clusters that can and/or cannot be further polymerized.

The term "hydrolytically stable" means that the monomer/precursor or nanogel/resin of the present disclosure in aqueous solution, will not undergo substantial degradation at pH in a range of about 1.0 to about 3.0 and at temperatures up to 30 degrees Celsius.

While reproducing nanogels based on UDMA/IBMA, some potential issues were encountered related to batch process of nanogel formation, in other words scaling up processes that are known in the art were not successful in producing useable nanogel compounds. For example, rapid increase in polymerization rate was observed when increasing batch size, and limited copolymerization for UDMA/IBMA, lower yield, difficulty in control over particle size and particle solubility, etc., were all observed when attempts at increasing batch size were attempted.

It is an object of the present disclosure to develop an optimized reaction process to address the issues revealed during batch processing in order to produce a nanogel with well-controlled quality at a reasonable cost. It is another object of this disclosure to explore the feasibility in making polymerizable antibacterial nanogel resin by incorporating antibacterial resins into nanogel.

It is also highly desirable to have hydrolytically-stable resins as hydrolytically stable monomers and hydrolytically stable antibacterial nanogel resins. The polymerizable acrylamide resins are known for its hydrolytic stability and N-substituted acrylamide resins were also known for its improved water solubility.

It is desired that polymerizable antibacterial nanogel resin and hydrolytically stable antibacterial nanogel, especially derived from charged nanogel would be highly effective in killing a broad spectrum of oral bacteria, especially those bacteria that are instrumental in early oral biofilm colonizer and the later oral biofilm colonizers or cariogenic bacteria. In additions its non-leachable feature would further get enhanced for such new polymerizable antibacterial nanogel resin, which would ensure low dose loading without jeopardizing mechanical integrity for the formulated dental products.

Disclosed herein are a polymerizable antibacterial nanogels and hydrolytically stable antibacterial nanogels and methods of making and using such polymerizable antibacterial nanogels and hydrolytically stable antibacterial nanogels as an additive to a dental product such as a resin monomer, cement, adhesive and composite formulations.

Polymerizable Antibacterial Nanogel

In an aspect of the present disclosure there is provided a polymerizable antibacterial nanogel derived from a monomer mixture comprising: (a) a polymerizable antibacterial monomer having at least one of imidazolium, pyridinium, ammonium or sulfonium group and at least one ethylenically unsaturated group; (b) at least one polymerizable resin monomer having at least one (meth)acrylate or (meth)acrylamide group; (c) at least one chain transfer agent; and (d) an initiator.

In one embodiment of the polymerizable antibacterial nanogel disclosed herein, the polymerizable antibacterial monomer comprises a compound of Formula I

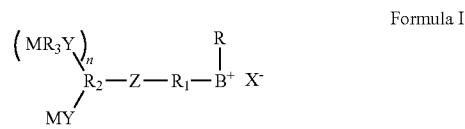

Formula I wherein,
M is vinylether, vinylester, vinylamine, allyl, acrylamide, methacrylamide, acrylate, or methacrylate moiety;
Y and Z are an independently a same or different alkylene, oxyalkylene, aminoalkylene or thioalkylene having from 1 to 4 carbons, arylene, carbonate, carboxylate, ester group, amide or a direct bond;
$R_1$ is a divalent hydrocarbon radical having from 2 to 18 carbons;
$R_2$ and $R_3$ are an independently a same or different straight or branched chain alkylene having from 1 to 4 carbons or a direct bond;
B is an imidazolium, pyridinium, ammonium or sulfonium group;
R is a linear or branched alkyl having from 4 to 16 carbon atoms or a direct bond;
X is a counter ion moiety; and
n is an integer of from 0 to 4.

In certain embodiment of the polymerizable antibacterial nanogel disclosed herein, the polymerizable antibacterial monomer comprises a compound of Formula II

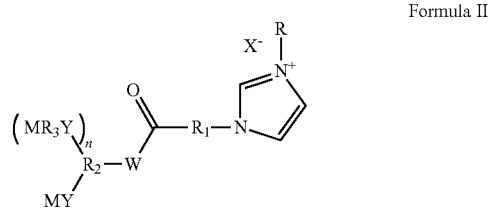

Formula II wherein
M is vinylether, vinylester, vinylamine, allyl, acrylamide, methacrylamide, acrylate, or methacrylate moiety;
Y is an alkylene, oxyalkylene or thioalkylene having from 1 to 4 carbons, carbonate, carboxylate, ester group, or direct bond;
W is O, $NR_4$ or a direct bond;
$R_1$ is a divalent hydrocarbon radical having from 2 to 18 carbons;
$R_2$ and $R_3$ are an independently a same or different straight or branched chain alkylene having from 1 to 4 carbons;
$R_4$ is an alkyl having from 1 to 4 carbons or $R_2M$;
R is a linear or branched alkyl having from 4 to 16 carbon atoms;
X is a counter ion moiety; and
n is an integer of from 0 to 1.

In certain embodiments of the polymerizable antibacterial nanogel, the polymerizable antibacterial monomer is a compound of formula II, where n is 1.

In certain embodiments of the polymerizable antibacterial nanogel, the polymerizable antibacterial monomer of compound of formula II, where n is 1 is a dimethacrylate of Formula:

In one embodiment of the polymerizable antibacterial nanogel, the polymerizable antibacterial monomer is a compound of formula II, where n is 0, the polymerizable antibacterial monomer is present in a concentration range of from 5 to 95 mole percent based on total moles of the monomer mixture; alternatively, in the range of from 10 to 70 mole percent based on total moles of the monomer mixture.

Hydrolytically Stable Polymerizable Resins and Antibacterial Monomers

One aspects of the present disclosure relates to method development, from which polymerizable resins are prepared respectively as hydrolytically stable and water soluble polymerizable resins, involving selective addition of Michael donors including thiols, amines, imidazole with asymmetric polyacrylamides as Michael acceptor to yield mono-substituted asymmetric polyacrylamides.

In embodiments, hydrolytically stable asymmetric polyacrylamide derived polymerizable resins and polymerizable monomer containing asymmetric polyacrylamide are used interchangeably.

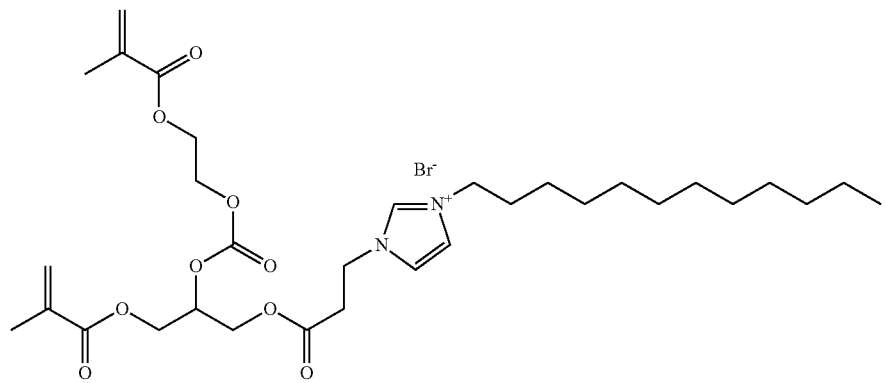 [SMILES: C=C(C)C(=O)OCCOC(=O)OC(COC(=O)CCn1cc[n+](CCCCCCCCCCCC)c1)COC(=O)C(=C)C ; [Br-]]

In one embodiment of the polymerizable antibacterial nanogel, the polymerizable antibacterial monomer is a compound of formula II, where n is 1, the polymerizable antibacterial monomer is present in a concentration range of from 5 to 45 mole percent based on total moles of the monomer mixture; alternatively in the range of from 10 to 30 mole percent based on total moles of the monomer mixture.

In certain embodiments of the polymerizable antibacterial nanogel, the polymerizable antibacterial monomer is a compound of formula II, where n is 0.

In certain embodiments of the polymerizable antibacterial nanogel, the polymerizable antibacterial monomer of compound of formula II, where n is 0 is a mono methacrylate having Formula:

In certain embodiments of the method development for hydrolytically stable asymmetric polyacrylamide derived polymerizable resins, the asymmetric polyacrylamide is compound of general formula

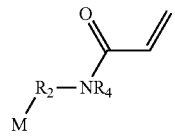

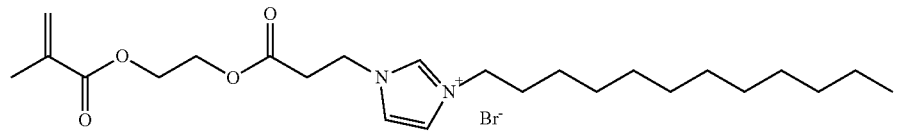

wherein

M is allyl, acrylamide, or methacrylamide moiety;

R$_2$ is an independently a same or different straight or branched chain alkylene having from 1 to 4 carbons;

R$_4$ is an alkyl having from 1 to 4 carbons or R$_2$M.

In a more specific embodiment, the asymmetric polyacrylamides is selected from

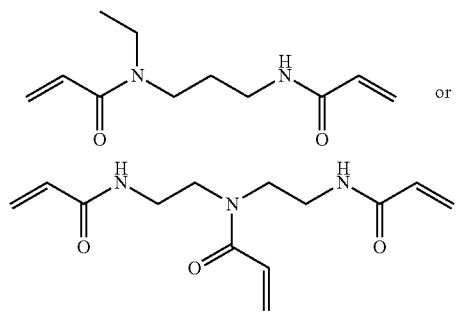

In certain embodiments of the method development for hydrolytically stable asymmetric polyacrylamide derived polymerizable resins, the mono-substituted asymmetric polyacrylamide is a compound of Formula

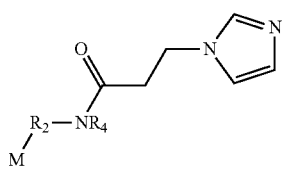

wherein

M is allyl, acrylamide, or methacrylamide moiety;

R$_2$ is an independently a same or different straight or branched chain alkylene having from 1 to 4 carbons;

R$_4$ is an alkyl having from 1 to 4 carbons or 13$_2$M.

It was surprisingly discovered that there was significant difference in reactivity of N-disubstituted acrylamide vs N-monosubstituted acrylamide in an unsymmetrical polyacrylamides towards Michael donors, for example, imidazole or thiols. It was discovered that highly selective Michael addition could be readily achieved with dominant addition of Michael donor towards the N-substituted acrylamides.

Imidazole or thiols could be added selectively to the N-substituted acrylamide as shown below:

Scheme-1

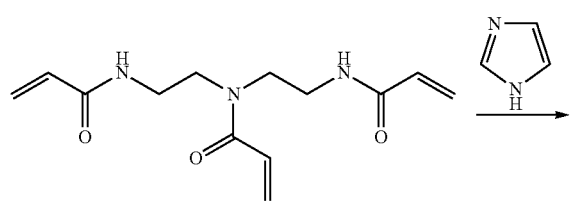

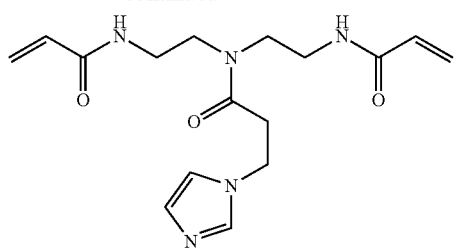

XJ10-123

Scheme-2

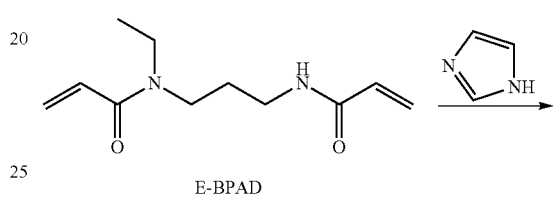

E-BPAD

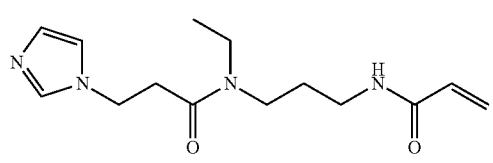

ABR-HS2

Hydrolytically stable asymmetric polyacrylamide derived polymerizable resin are soluble in water or a mixture of water and another one or more organic solvents. In some embodiments the organic water-soluble solvent is water mixed with ethanol, propanol, butanol, acetone, and/or methyl ethyl ketone.

The term "hydrolytically stable asymmetric polyacrylamide derived polymerizable resin" means that the monomer/resin of the present disclosure in aqueous solution, will not undergo substantial degradation at pH in a range of about 1.0 to about 3.0 and at temperatures up to 30 degrees Celsius.

In some embodiment, the hydrolytically stable asymmetric polyacrylamide derived polymerizable resin contain at least one moiety selected from imidazolium for capability to killing microbes/bacteria.

In certain embodiment, the hydrolytically stable asymmetric polyacrylamide derived polymerizable resin containing imidazolium moiety is a polymerizable antibacterial monomer for polymerizable antibacterial nanogel.

In an exemplary embodiments of the polymerizable antibacterial nanogel, the polymerizable antibacterial monomer of compound of formula II, where n is 0, Y is direct bond and W is NR$_4$ is an amide of Formula III:

Formula III

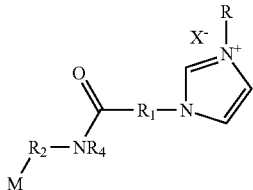

wherein
M is allyl, acrylamide, or methacrylamide moiety;
$R_1$ is a divalent hydrocarbon radical having from 2 to 18 carbons;
$R_2$ is an independently a same or different straight or branched chain alkylene having from 1 to 4 carbons;
$R_4$ is an alkyl having from 1 to 4 carbons or $R_2M$;
R is a linear or branched alkyl having from 4 to 16 carbon atoms; and
X is a counter ion moiety.

Example of compound of Formula III may include acrylamide of formula:

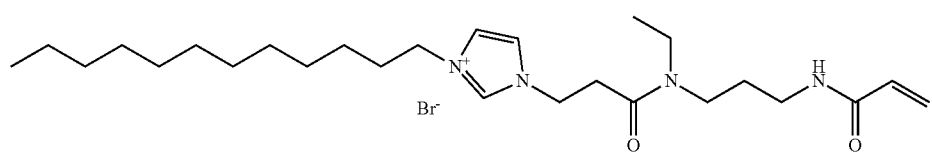 [SMILES: C=CC(=O)NCCCN(CC)C(=O)CCn1cc[n+](CCCCCCCCCCCC)c1 ; [Br-]]

In one embodiment of method of forming a hydrolytically stable, water soluble polymerizable antibacterial monomer containing asymmetric polyacrylamides, the method comprises steps of:
(a) reacting an asymmetric polyacrylamide in the presence of a Michael donor under conditions selected to yield mono-substituted asymmetric polyacrylamide; wherein the Michael donor is imidazole;
(b) converting the imidazole of mono-substituted asymmetric polyacrylamide monomer to an imidazolium to yield the hydrolytically stable, water soluble polymerizable antibacterial monomer containing asymmetric polyacrylamides of Formula

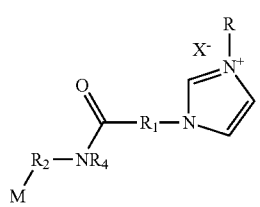

wherein;
M is allyl, acrylamide, or methacrylamide moiety;
$R_1$ is a divalent hydrocarbon radical having from 2 to 18 carbons;
$R_2$ is an independently a same or different straight or branched chain alkylene having from 1 to 4 carbons;
R is a linear or branched alkyl having from 4 to 16 carbon atoms; and
$R_4$ is an alkyl having from 1 to 4 carbons or $R_2M$.

In certain embodiment of method of forming a hydrolytically stable, water soluble polymerizable antibacterial containing asymmetric polyacrylamides, the asymmetric polyacrylamides is compound of general formula

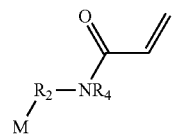

wherein
M is allyl, acrylamide, or methacrylamide moiety;
$R_2$ is an independently a same or different straight or branched chain alkylene having from 1 to 4 carbons; and
$R_4$ is an alkyl having from 1 to 4 carbons or $R_2M$.

In certain embodiment of method of forming a hydrolytically stable, water soluble polymerizable antibacterial containing asymmetric polyacrylamides, the mono-substituted asymmetric polyacrylamide monomer is a compound of Formula

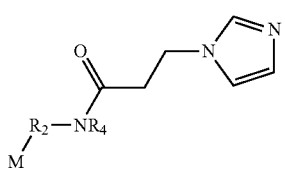

wherein
M is allyl, acrylamide, or methacrylamide moiety;
$R_2$ is an independently a same or different straight or branched chain alkylene having from 1 to 4 carbons; and
$R_4$ is an alkyl having from 1 to 4 carbons or $R_2M$.

In certain embodiment of method of forming a hydrolytically stable, water soluble polymerizable antibacterial containing asymmetric polyacrylamides, the step of converting the imidazole of mono-substituted asymmetric polyacrylamide monomer to an imidazolium comprises reacting mono-substituted asymmetric polyacrylamide monomer with RX; wherein R is a linear or branched alkyl having from 4 to 16 carbon atoms; and X is a counter ion moiety.

In one specific embodiment, the step of converting the imidazole of mono-substituted asymmetric polyacrylamide monomer to an imidazolium include following reaction:

Scheme-3

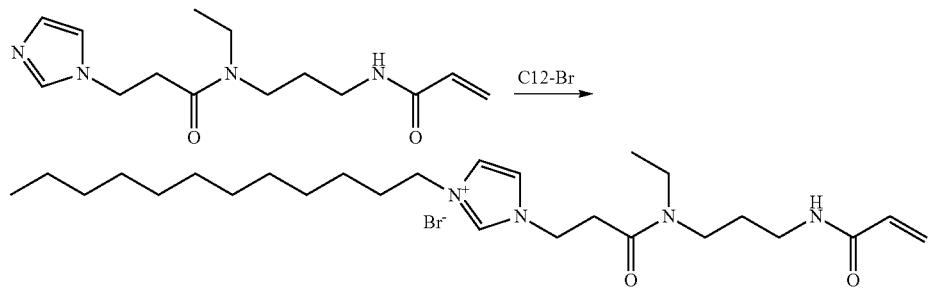

ABR-HS3/XJ10-118
Molecular Weight = 527.59
Molecular Formula = $C_{26}H_{47}N_4O_2Br$ Polymerizable Resin Monomer In certain embodiments of the polymerizable antibacterial nanogel, the polymerizable resin monomer having at least one (meth) acrylate or (meth)acrylamide group is selected from the group consisting of mono-, di-, tri- or tetra functional monomer.

Examples of monofunctional (meth)acrylate monomer include $C_1$-$C_{20}$ alkyl(meth)acrylates such as methyl (meth)acrylate, ethyl (meth)acrylate, isopropyl (meth)acrylate, propyl(meth)acrylate, isobutyl(meth)acrylate, hexyl(meth)acrylate, cyclo hexyl (meth)acrylate, lauryl(meth)acrylate, cetyl (meth)acrylate, stearyl (meth)acrylate and isobornyl (meth)acrylate.

Examples of difunctional (meth)acrylate monomer include, but are not limited to, ethyleneglycoldi(meth)acrylate, diethyleneglycoldi(meth)acrylate, triethyleneglycoldi(meth)acrylate, butyleneglycoldi(meth)acrylate, tetraethyleneglycoldi(meth)acrylate, polyethylene glycol di(meth)acrylate, neopentlyglycoldi(meth)acrylate, 1,6-hexanediol di(meth)acrylate, 1,10-decanediol di(meth)acrylate, 2,2-bis[4-[3-(meth)acryloyloxy-2-hydroxypropoxy]phenyl]propane(bis-GMA), 2,2-bis[4-(meth)acryloyloxyethoxyphenyl] propane, 2,2-bis[4-(meth)acryloyloxypolyethoxyphenyl] propane, 1,2-bis[3-(meth)acryloyloxy-2-hydroxypropoxy] ethane, pentaerythritol di(meth)acrylate, and [2,2,4-trimethylhexamethylenebis(2-carbamoyloxyethyl)] dimethacrylate (commonly known as urethane dimethacrylate or UDMA).

Examples of trifunctional (meth)acrylate monomer include, but are not limited to, trimethylolpropanetri(meth)acrylate, trimethylolethane tri(meth)acrylate, trimethylolmethane tri(meth)acrylate, and pentaerythritol tri(meth)acrylate.

An example of tetratrifunctional (meth) acrylate is pentaerythritol tetra(meth)acrylate.

Examples of a methacrylamide monomer include (meth) acrylamide, N-methyl(meth)acrylamide, N-ethyl(meth)acrylamide, N,N-dimethyl(meth)acrylamide, N,N-diethyl (meth)acrylamide, N,N-methylethyl(meth)acrylamide and N,N-methylene-bis(meth)acrylamide.

Examples of an acrylamide monomer include, but are not limited to, N-butylacrylamide, diacetoneacrylamide, N, N-dimethylacrylamide, and N, N-dibenzylacrylamide.

In certain embodiments of the polymerizable antibacterial nanogel disclosed herein, the polymerizable monomer include, but not limited to, 2,2'-bis [4-(3-methacryloxy-2-hydroxy propoxy)-phenyl] propane (bis-GMA), tetraethyleneglycoldi(meth)acrylate (TEGDMA), urethane dimethacrylate (UDMA), trimethylolpropane trimethacrylate, $C_1$-$C_{20}$ alkyl(meth)acrylates, an aromatic methacrylate, a hydroxy alkyl (meth)acrylate and a (meth)acrylamide.

In one embodiment of the polymerizable antibacterial nanogel, the at least one ethylenically unsaturated group of the polymerizable antibacterial monomer is a methacrylate group and at least one (meth)acrylate group of polymerizable resin monomer is a methacrylate group such that a combination of methacrylate group of the polymerizable antibacterial monomer and the methacrylate group of the polymerizable resin monomer is present in a range of from 50 to 90 mole percent based on total moles of the monomer mixture; more preferably of from 60 to 80 mole percent based on total moles of the monomer mixture.

In certain embodiments of the polymerizable antibacterial nanogel, the polymerizable resin monomer is $C_1$-$C_{20}$ alkyl (meth)acrylates.

Examples of $C_1$-$C_{20}$ alkyl(meth)acrylates includes but not limited to methyl (meth)acrylate, ethyl (meth)acrylate, isopropyl (meth)acrylate, propyl(meth)acrylate, isobutyl(meth)acrylate, hexyl(meth)acrylate, cyclo hexyl (meth)acrylate, lauryl(meth)acrylate, cetyl (meth)acrylate, stearyl (meth)acrylate and isobornyl (meth)acrylate.

In a more specific embodiment of the polymerizable antibacterial nanogel, the $C_1$-$C_{20}$ alkyl(meth)acrylates is isobornyl methacrylate.

In certain embodiments of the polymerizable antibacterial nanogel, the polymerizable resin monomer is an aromatic (meth) acrylate.

Examples of aromatic (meth)acrylates may include, but are not limited to, 2-phenoxyethyl(meth)acrylate, phenyl (meth)acrylate, benzoyl(meth)acrylate, benzyl (meth)acrylate, 2-phenylethyl (meth)acrylate, 3-phenylpropyl(meth) acrylate, 4-phenylbutyl (meth)acrylate, 4-methylphenyl (meth)acrylate, 4-methylbenzyl (meth)acrylate, and 2-(4-methoxyphenyl)ethyl methacrylate.

In a more specific embodiment of the polymerizable antibacterial nanogel, the aromatic (meth)acrylate is selected from the group consisting of 2-phenoxyethyl(meth)acrylate, phenyl (meth)acrylate and benzoyl(meth)acrylate.

In certain embodiments of the polymerizable antibacterial nanogel, the polymerizable resin monomer is hydroxyl alkyl acrylate, hydroxyl alkyl methacrylate, hydroxyl alkyl acrylamide or hydroxyl alkyl (meth)acrylamide.

Examples of hydroxyalkylmethacrylate may include, but are not limited to, hydroxyethyl (meth)acrylate (HEMA), polyethoxyethyl methacrylate, hydroxypropyl methacrylate and hydroxybutylmethacrylate, 6-hydroxyhexyl (meth)acrylate, and 10-hydroxydecyl(meth)acrylate.

Examples of hydroxyalkyl acrylamide may include, but are not limited to, hydroxyethyl acrylamide, N-tris(hydroxymethyl)methyl)acrylamide, N-(hydroxymethyl)acrylamide or a combination thereof.

Examples of hydroxylalkyl methacrylamide may include, but are not limited to, N-methylol(meth)acrylamide, hydroxyethyl(meth)acrylamide, and N,N-Bis-(2-hydroxyethyl)methacrylamide.

In certain embodiments of the polymerizable antibacterial nanogel deisclosed herein, a chain transfer agent may be included.

The chain transfer agent may be used to afford shorter polymer chains that delays macrogel formation. The chain transfer agent may be chosen from a range of thiol compounds including propyl mercaptan, butyl mercaptan, hexyl mercaptan, 1-dodecanethiol, mercaptoethanol and combinations thereof.

In one particular embodiment the polymerizable antibacterial nanogel, the chain transfer agent may be 1-dodecanethiol.

The amount of chain transfer agent may be present of from 10 to 50% (mole/mole) of the total (meth)acrylate in the monomer mixture. In one particular embodiment, the amount of chain transfer agent may be present of from 25 to 35% (mol/mole) of the total ethylenically unsaturated group in the monomer mixture.

In certain embodiments of the polymerizable antibacterial nanogel, an initiator may be included.

The polymerization of the monomers may be initiated by thermally induced decomposition of thermal initiator such as an azo compound or an organic peroxides.

In one embodiment the azo initiators are azobis(isobutyronitrile), azobis 2(methylbutyronitrile), azobis (2,4-dimethylvaleronitrile). In one particular embodiment, initiator is azobis (isobutryonitrile).

In one embodiment the organic peroxides may be selected from the group consisting of dicumylperoxide, di-tert-butylperoxide, tert-butylperoxybenzoate, tert-butyl peroxyneodecanoate, tert-butylperoxypivalate, tert-butylperoxyisobutyrate; isononanoyl peroxide (Cat K); didecanoylperoxide, benzoylperoxide, lauroylperoxide; dimyristyl peroxydicarbonate, di(2-ethylhexyl) peroxydicarbonate and dicetylperoxydicarbonate.

The polymerization of the monomers may also be initiated with redox initiator systems.

In one embodiment the redox initiators may be benzoylperoxide and tertiary amines, for example, benzoyl peroxide and ethyl 4-N,N'-dimethylaminobenzoate (EDAB); hydrogen peroxide and ferrous salt; persulfate (potassium persulfate) and peroxide (t-butyl hydroperoxide) initiators with other reductants, such as sodium metabisulfite, may also be used as redox initiator systems. In addition, numerous reducing agents like alcohols, thiols, ketones, aldehydes, acids, amines and amides may be been used in combination with oxidizing metal ions to participate in general single-electron transfer reactions for free radical polymerization. Metal ions used mainly for this purpose is selected from the group consisting of Mn(III) (and Mn(VII)), Ce(IV), V(V), Co(III), Cr(VI) and Fe(III).

The thermal initiator may be present in amount of from 0.01 to 7% w/w of total (methacrylate) in the monomer mixture, and more specifically of from 0.2 to 5% w/w and more specifically, of from 0.5 to 2.0% w/w of total ethylenically unsaturated group in the monomer mixture.

In an aspect of the present disclosure, a method of preparing the polymerizable antibacterial nanogels are described.

The polymeric antibacterial nanogel may be prepared by redox initiator systems and light-induced radical polymerization at ambient temperature or microwave synthesis with precise temperature control.

In one embodiment, the polymeric antibacterial nanogel may be prepared in a microwave reactor with precise temperature control. In one embodiment, the monomers are mixed at temperature of 100° C.

A mixture of a polymerizable antibacterial monomer having at least one of imidazolium, pyridinium, ammonium or sulfonium group and at least one (meth)acrylate group, at least one polymerizable resin monomer having at least one (meth)acrylate or (meth)acrylamide group, at least one chain transfer agent, and an initiator were placed in a microwave reactor in the presence of a solvent.

The solvents to be used in preparation of the antibacterial nanogel should be an inert solvent. Suitable solvents would be the ones in which monomers dissolve, such as dipolar aprotic solvents such as methyl ethyl ketone or dimethyl sulfoxide, ketones such as acetones, 2-butanone, or cyclohexanone, hydrocarbons such as toluene and xylene, ether such as dioxane or tetrahydrofuran. In one aspect, a particular nanogel preparation can be more efficiently prepared than another. For example, improved solubility of the nanogel was achieved in methyl ethyl ketone rather than toluene (See table 3), which is critical for redispersibility of such a nanogel in a resin matrix.

The reaction temperature may be, for example from 20 to 120° C., such as from 65° C. to 85° C. The reaction time may be in the range of about 5 to 15 min.

Dental Composition: Additive in Resin Monomer, Cement, Adhesive, Composite Formulation Dental compositions disclosed herein may be composed of (a) a polymerizable antibacterial nanogel (b) a polymerizable resin, (c) an initiator; (d) filler particles (e) a stabilizer and (f) other additives.

In one embodiment of the dental composition, the polymerizable antibacterial nanogel may be present in an amount of from 0.5 weight percent to about 90 weight percent of the dental composition.

Polymerizable Resin

In one embodiment of the dental composition, the polymerizable resin may be present in an amount of from 10 weight percent to about 95 weight percent of the dental composition.

Polymerizable resin may be selected from the group consisting of acrylates, methacrylates, ethylenically unsaturated compounds, carboxyl group-containing unsaturated monomers, $C_{2-8}$ hydroxyl alkyl esters of (meth)acrylic acid, $C_{1-24}$ alkyl esters or cycloalkyl esters of (meth)acrylic acid, $C_{2-18}$ alkoxyalkyl esters of (meth)acrylic acid, olefins or diene compounds, monoesters/diesters, monoethers, adducts, TPH resin, SDR Resin and/or BPA-free resins.

Examples of specific acrylate resins include, but are not limited to, methyl acrylate, ethyl acrylate, propyl acrylate, isopropyl acrylate, 2-hydroxyethyl acrylate, hydroxypropyl acrylate, tetrahydrofurfuryl acrylate, glycidyl acrylate, glycerol mono- and di-acrylate, ethyleneglycol diacrylate, polyethyleneglycol diacrylate, neopentyl glycol diacrylate, trimethylolpropane triacrylate, mono-, di-, tri-acrylate, mono-, di-, tri-, and tetra-acrylates of pentaerythritol and dipentaerythritol, 1,3-butanediol diacrylate, 1,4-butanedioldiacrylate, 1,6-hexane diol diacrylate, 2,2'-bis[3(4-phenoxy)-2-hydroxypropane-1-acrylate]propane, 2,2'-bis(4-acryloxyphenyl)propane, 2,2'-bis[4(2-hydroxy-3-acryloxyphenyl)propane, 2,2'-bis(4-acryloxyethoxyphenyl)propane, 2,2'-bis(4-acryloxypropoxyphenyl)propane, 2,2'-bis(4-acryloxydiethoxyphenyl)propane, and dipentaerythritol pentaacrylate esters.

Examples of specific conventional methacrylate resins may include, but are not limited to, methyl methacrylate, ethyl methacrylate, propyl methacrylate, isopropyl methacrylate, tetrahydrofurfuryl methacrylate, glycidyl methacrylate, the diglycidyl methacrylate of bis-phenol A (2,2-Bis[4-(2-hydroxy-3-methacryloxypropoxy)phenyl]propane) (BisGMA), glycerol mono- and di-methacrylate, ethyleneglycol dimethacrylate, polyethyleneglycol dimethacrylate, triethylene glycol dimethacrylate (TEGDMA), neopentylglycol dimethacrylate, trimethylol propane trimethacrylate, mono-, di-, tri-, and tetra-methacrylates of pentaerythritol and dipentaerythritol, 1,3-butanediol dimethacrylate, 1,4-butanediol dimethacrylate, Bis[2-(methacryloyloxy)ethyl]phosphate (BisMEP),1,6-hexanediol dimethacrylate, 2,2'-bis(4-methacryloxyphenyl)propane, 2,2'-bis[4(2-hydroxy-3-methacryloxy-phenyl)]propane, 2,2'-bis(4-methacryloxyethoxyphenyl)propane, 2,2'-bis(4-methacryloxypropoxyphenyl)propane, 2,2'-bis(4-methacryloxydiethoxyphenyl)propane, and 2,2'-bis[3(4-phenoxy)-2-hydroxypropane-1-methacrylate]propane.

Examples of ethylenically unsaturated compounds may include, but are not limited to, acrylic acid esters, methacrylic acid esters, hydroxy-functional acrylic acid esters, hydroxy-functional methacrylic acid esters, halogen and hydroxy containing methacrylic acid esters and combinations thereof. Such free radically polymerizable compounds include n-, -, sec-, or t-butyl methacrylate, hexyl methacrylate, 2-ethylhexyl methacrylate, octylmethacrylate, decyl methacrylate, lauryl methacrylate, cyclohexyl methacrylate, stearyl methacrylate, allyl(meth)acrylate, glycerol tri(meth)acrylate, diethyleneglycol di(meth)acrylate, triethyleneglycol di(meth)acrylate, 1,3-propanediol di(meth)acrylate, trimethylolpropane tri(meth)acrylate, 1,2,4-butanetriol tri(meth)acrylate, 1,4-cyclohexanediol di(meth)acrylate, pentaerythritol tetra(meth)acrylate, sorbitol hex(meth)acrylate, tetrahydrofurfuryl(meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenol A di(meth)acrylate, trishydroxyethyl-isocyanurate tri(meth)acrylate; (meth)acrylamides (i.e., acrylamides and methacrylamides) such as (meth)acrylamide, methylene bis-(meth)acrylamide, and diacetone (meth)acrylamide; urethane (meth)acrylates; urethane modified BisGMA dimethacrylate resin, the bis-(meth)acrylates of polyethylene glycols, and chlorine-, bromine-, fluorine-, and hydroxyl group containing monomers, for example, 3-chloro-2-hydroxylpropyl (meth)acrylate.

Examples of carboxyl group-containing unsaturated monomers may include, but are not limited to, such as acrylic acid, methacrylic acid, crotonic acid, itaconic acid, maleic acid, and fumaric acid.

Examples of $C_{2-8}$ hydroxyl alkyl esters of (meth)acrylic acid may include but are not limited to 2-hydroxyethyl (meth)acrylate, 2-hydroxylpropyl (meth)acrylate, 3-hydroxypropyl (meth)acrylate, and hydroxybutyl (meth)acrylate.

Examples of $C_{2-18}$ alkoxyalkyl esters of (meth)acrylic acid may include, but are not limited to, methoxybutyl methacrylate, methoxyethyl methacrylate, ethoxyethyl methacrylate, and ethoxybutyl methacrylate.

Olefins or diene compounds may include, but are not limited to, ethylene, propylene, butylene, isobutene, isoprene, chloropropene, fluorine containing olefins and vinyl chloride.

Examples of monoesters may include monoesters between a polyether polyol (e.g., polyethylene glycol, polypropylene glycol or polybutylene glycol) and an unsaturated carboxylic acid (preferably methacrylic acid), monoesters or diesters between an acid anhydride group-containing unsaturated compounds (e.g., maleic anhydride or itaconic anhydride) and a glycol (e.g. ethylene glycol, 1,6-hexanediol or neopentyl glycol).

Example of monoethers may include monoethers between a polyether polyol (e.g., polyethylene glycol, polypropylene glycol or polybutylene glycol) and a hydroxyl group-containing unsaturated monomer (e.g., 2-hydroxyl methacrylate).

Examples of adducts may include, but are not limited to, adducts between an unsaturated carboxylic acid and a monoepoxy compound; adducts between glycidyl (meth)acrylates (preferably methacrylate) and a monobasic acid (e.g., acetic acid, propionic acid, p-t-butylbenzonic acid or a fatty acid).

Initiators

Initiators are often used in chain-growth polymerization such as radical polymerization to regulate initiation by heat or light.

Thermal polymerization initiators are compounds that generate radicals or cations upon exposure to heat. For example, azo compounds such as 2,2'-azobis(isobutyronitrile) (AIBN) and organic peroxides such as benzoyl peroxide (BPO) are well-known thermal radical initiators, and benzenesulfonic acid esters and alkylsulfonium salts have been developed as thermal cation initiators. Organic and inorganic compounds can be used to generate radicals that initiate polymerizations. Radicals may be generated by thermal or ambient redox conditions. Decomposition rates for some initiators vary with pH and the presence of amines.

Additional free radical initiators may include organic photoinitiators. Suitable photoinitiators include Type I and Type II. They can be used independently or as mixture of different photoinitiators plus additional co-initiators. Suitable photosensitizers may include monoketones and diketones (e.g. alpha diketones) that absorb some light within a range of about 300 nm to about 800 nm (such as, about 400 nm to about 500 nm) such as camphorquinone, benzil, furil, 3,3,6,6-tetramethylcyclohexanedione, phenanthraquinone and other cyclic alpha diketones. In embodiments, the initiator is camphorquinone. Examples of electron donor compounds include substituted amines, e.g., ethyl 4-(N, N-dimethylamino)benzoate as the accelerator.

Other suitable photoinitiators for polymerizing free radically photopolymerizable compositions may include the class of phosphine oxides that typically have a functional wavelength range of about 380 nm to about 1200 nm. In embodiments, phosphine oxide free radical initiators with a functional wavelength range of about 380 nm to about 450 nm are acyl and bisacyl phosphine oxides.

Commercially available phosphine oxide photoinitiators capable of free-radical initiation when irradiated at wavelength ranges of greater than about 380 nm to about 450 nm may include 1-hydroxy cyclohexyl phenyl ketone (IRGACURE 184), 2,2-dimethoxy-1,2-diphenylethan-1-one (IRGACURE 651), bis(2,4,6-trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl) butanone (IRGACURE 369), 2-methyl-1-[4-(methylthio) phenyl]-2-morpholinopropan-1-one (IRGACURE 907), and 2-hydroxy-2-methyl-1-phenyl propan-1-one (DAROCUR 1173). bis(2,4,6-trimethylbenzoyl) phenyl phosphine oxide (IRGACURE 819), bis(2,6-dimethoxybenzoyl)-(2,4,4-trimethylpentyl) phosphine oxide (CGI 403), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700), a 1:1 mixture, by weight, of bis(2,4,6-trimethylbenzoyl)phenyl phosphine oxide and 2-hydroxy-2-methyl-1-phenylpropane-1-one (DAROCUR 4265), and ethyl 2,4,6-trimethylbenzylphenyl phosphinate (LUCIRIN LR8893X).

In one embodiment of the dental composition, the initiator may be present in an amount of from 0.001 weight percent to about 5 weight percent of the dental composition.

Fillers

The dental composition of the present disclosure may include fillers.

Examples of suitable filler particles include, but are not limited to, strontium silicate, strontium borosilicate, barium silicate, barium borosilicate, barium fluoroalumino borosilicate glass, barium alumino borosilicate, calcium silicate, calcium alumino sodium fluoro phosphor-silicate lanthanum silicate, alumino silicate, and the combination comprising at least one of the foregoing fillers. The filler particles can further comprise silicon nitrides, titanium dioxide, fumed silica, colloidal silica, quartz, kaolin ceramics, calcium hydroxy apatite, zirconia, and mixtures thereof. Examples of fumed silica include OX-50 from DeGussa AG (having an average particle size of 40 nm), Aerosil R-972 from DeGussa AG (having an average particle size of 16 nm), Aerosil 9200 from DeGussa AG (having an average particle size of 20 nm), other Aerosil fumed silica might include Aerosil 90, Aerosil 150, Aerosil 200, Aerosil 300, Aerosil 380, Aerosil R711, Aerosil R7200, and Aerosil R8200, and Cab-O-Sil M5, Cab-O-Sil TS-720, Cab-O-Sil TS-610 from Cabot Corp.

The filler particles used in the composition disclosed herein may be surface treated before they are blended with organic compounds. The surface treatment using silane coupling agents or other compounds are beneficial as they enable the filler particles to be more uniformly dispersed in the organic resin matrix, and also improve physical and mechanical properties. Suitable silane coupling agents include 3-methacryloxypropyltrimethoxysilane, methacryloxyoctyltrimethoxysilane, styrylethyltrimethoxysilane, 3-mercaptopropyltrimethoxysilane, and mixtures thereof.

The filler particles can have a particle size of from about 0.002 microns to about 25 microns. In one embodiment, the filler can comprise a mixture of a micron-sized radiopaque filler such as barium alumino fluoro borosilicate glass (BAFG, having an average particle size of about 1 micron) with nanofiller particles, such as fumed silica such as OX-50 from Degussa AG (having an average particle size of about 40 nm). The concentration of micron-size glass particles can range from about 50 weight percent to about 75 weight percent of the antibacterial dental composition, and the nano-size filler particles can range from about 1 weight percent to about 20 weight percent of the antibacterial dental composition.

The dental composition of the present disclosure may be a composite, and may include a filler material in an amount from about 30 to about 90 percent by weight.

The dental composition of the present disclosure may be an adhesive, and may include a filler in an amount from about 50 to about 65 percent by weight.

The dental composition of the present disclosure may be a sealant, and may include filler in an amount from about 10 to about 50 percent by weight.

A dental composition according to the disclosure may be a cement, and may include filler in an amount from about 50 to about 90 percent by weight.

Fillers may be present in amounts of from about 40 weight percent to about 85 weight percent of the antibacterial dental composition, such as from about 45 weight percent to about 85 weight percent or from about 60 weight percent to about 80 weight percent of the antibacterial dental composition.

In formulated compositions, additional additives will be optionally included: ultra-violet stabilizers, fluorescent agents, opalescent agents, pigments, viscosity modifiers, fluoride-releasing agents, polymerization inhibitors, and the like. Typical polymerization inhibitors for a free radical system may include hydroquinone monomethyl ether (MEHQ), butylated hydroxytoluene (BHT), tertiary butyl hydro quinone (TBHQ), hydroquinone, phenol, butyl hydroxyaniline, and the like. The inhibitors act as free radical scavengers to trap free radicals in the composition and to extend the shelf life stability of the composition. The polymerization inhibitors, if present, may be present in amounts of from about 0.001 weight percent to about 1.5 weight percent of the antibacterial dental composition, such as from about 0.005 weight percent to about 1.1 weight percent or from about 0.01 weight percent to about 0.08 weight percent of antibacterial dental composition. The composition may include one or more polymerization inhibitors.

Use of Nanogels as Dental Composites

Antibacterial dental composite may be formulated by mixing antibacterial nanogel modified resin matrix and filler particles.

In certain embodiments of antibacterial dental composite, the antibacterial nanogel modified resin matrix comprises a polymerizable antibacterial nanogel, a polymerizable resin, an initiator and a stabilizer. The polymerizable antibacterial nanogel may be obtained from a mixture comprising a polymerizable antibacterial monomer having at least one of imidazolium, pyridinium, ammonium or sulfonium group and at least one ethylenically unsaturated group; at least one polymerizable resin monomer having at least one (meth) acrylate or (meth)acrylamide group; at least one chain transfer agent, and an initiator.

In one embodiment of the antibacterial dental composite, the anti-bacterial nanogel modified resin matrix is present in the composite in a concentration of from 0.5 to 10.0 weight percent based on a total weight of the composite; in a concentration of from 0.8 to 7 weight percent or in a concentration of from 1 to 3 weight percent based on a total weight of the composite.

The antibacterial dental composite composition disclosed herein further comprises one or more types of filler particles that are suitable for use in dental compositions. Filler particles are critical components to the composition described herein. Fillers that are suitable for use in the composition described herein providing the composite with desired physical and curing properties, such as increased strength, modulus, hardness, reduced thermal expansion and polymerization shrinkage, and also provide a stable shelf life such that no adverse reaction occurs between the filler particles with any of the resin matrix's organic compounds in composition during storage or transportation, and before the intended shelf-life is reached.

Examples of suitable filler particles, include, but are not limited to, BABG/999117, EG 9726/907645, Can-O-Sil TS720/431350, strontium silicate, strontium borosilicate, barium silicate, barium borosilicate, barium fluoroalumino borosilicate glass, barium alumino borosilicate, calcium silicate, calcium alumino sodium fluoro phosphor-silicate lanthanum silicate, alumino silicate, and the combination comprising at least one of the foregoing fillers. The filler particles can further comprise silicon nitrides, titanium dioxide, fumed silica, colloidal silica, quartz, kaolin ceramics, calcium hydroxy apatite, zirconia, and mixtures thereof. Examples of fumed silica include OX-50 from Degussa AG (having an average particle size of 40 nm), Aerosil R-972 from Degussa AG (having an average particle size of 16 nm), Aerosil 9200 from Degussa AG (having an average particle size of 20 nm), other Aerosil fumed silica might include Aerosil 90, Aerosil 150, Aerosil 200, Aerosil 300, Aerosil 380, Aerosil R711, Aerosil R7200, and Aerosil R8200, and Cab-O-Sil M5, Cab-O-Sil TS-720, Cab-O-Sil TS-610 from Cabot Corp.

The filler particles can have a particle size of from about 10 nm to about 50 microns.

In one embodiment of the antibacterial dental composite, filler particles may be present in a concentrations of from about 20 weight percent to about 95 weight percent based on a total weight of the composite, such as from about 30 weight percent to about 70 weight percent or from about 75 to about 95 weight percent based on a total weight of the composite.

In certain embodiments of the antibacterial dental composite, the antibacterial nanogel modified resin matrix comprises from about 0.5 weight percent to about 10 weight percent of the polymerizable antibacterial nanogel; from about 10 weight percent to about 95 weight percent of a polymerizable resin and from about 0.001 weight percent to about 5 weight percent of at least one of a photoinitiator, or a thermal/redox initiator.

In certain embodiments of the antibacterial dental composite, the stabilizer includes butylated hydroxy toluene (BHT).

In certain embodiments of the antibacterial dental composite, the photoinitiator includes camphoroquinone/EDAB.

Embodiments of the present disclosure provide antibacterial resin matrix that may be composed of antibacterial resin composition ZL1-077, polymerizable resin such as TPH resin/999446, camphoroquinone, EDAB and BHT.

Experimental Procedures

The following abbreviations may be used
UDMA: di(methacryloxyethyl)trimethyl-1,6-hexaethylenediurethane UDMA: di(methacryloxyethyl)trimethyl-1,6-hexaethylenediurethane

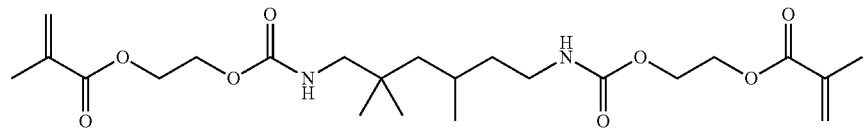

IBMA: isobornyl methacrylate

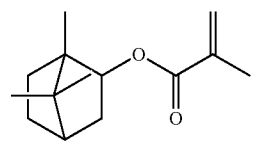

POEMA: 2-phenoxyethyl (meth)acrylate

HEMA: hydroxylethyl methacrylate

E-BPAD:

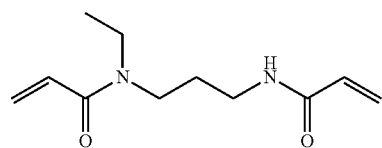

FFM3:

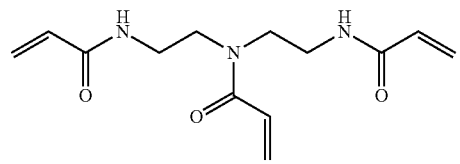

XJ10-123:

-continued

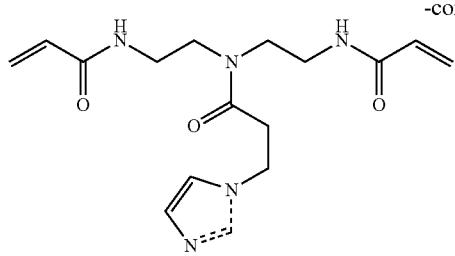

ABR-C or XJ9-28:

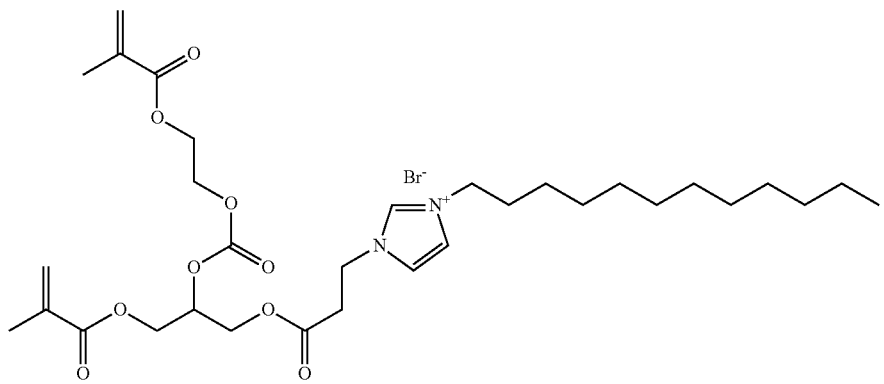

ABR-E or XJ8-160:

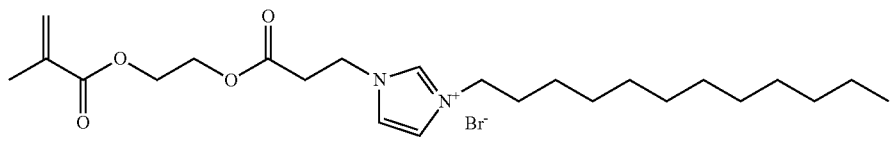

ABR-HS3/XJ10-118

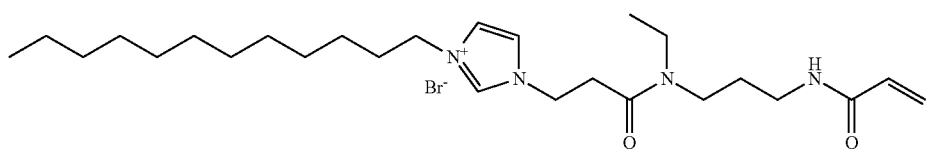

Experimental Method

NMR Analysis: 300 MHz NMR (Varian) was used to elucidate the structure and to monitor the reaction processing.

Flexural strength and modulus were tested according to ISO 4049, 2×2×25 mm specimens were cured by three overlapped spot curing with Spectrum 800 with 13 mm light guide at 800 mw/cm$^2$, 20" for each spot on one side only. The cured specimens (6-10) were placed in deionized water and stored at 37° C. for 24 h, then were sanded prior to the test at room temperature.

Compressive strength and modulus were tested according to ISO 9917, which is actually for water-based cements since ISO 4049 does not specify for compressive strength. φ4×6 mm glass slave as mold for specimen preparation (6). It was cured by Spectrum 800 at 800 mw/cm$^2$ from both top and bottom, at 20" each. The cured specimens (6-10) were placed in deionized water and stored at 37° C. for 24 hrs, and then were sanded prior to the test at room temperature.

Polymerization Shrinkage was calculated from the density change before and after curing, which were measured by helium pycnometer at room temperature. New KN/CK shrinkage test protocol was followed in this test: 3 pieces of round disc samples from a φ10×2 mm Teflon mold. It was pressed between Mylar films and cured by Spectrum 800 at 800 mw/cm$^2$ for 20 seconds from top and bottom sides, respectively. The cured specimen is stored at room temperature for 2-3 hrs or for 24 hrs prior to the density measurement.

Shrinkage Stress was measured by using NIST/ADA's tensometer. Specimen with 2.25 mm in thickness (c-factor as 1.33) is cured for 60 seconds by DENTSPLY/Cauk's QHL light at 550 mw/cm2. The total stress at the 60th minute is taken to rank different materials.

UV-Vis Spectroscopy was measured by using Thermo Scientific's Evolution 160 UV-Vis spectrometer. Thin film of 25-200 microns was casted directly onto a fused silica plate with a specially-fabricated stage.

Synthetic Procedure for Hydrolytically Stable Polymerizable Resins (XJ10-123)

Figure 4:
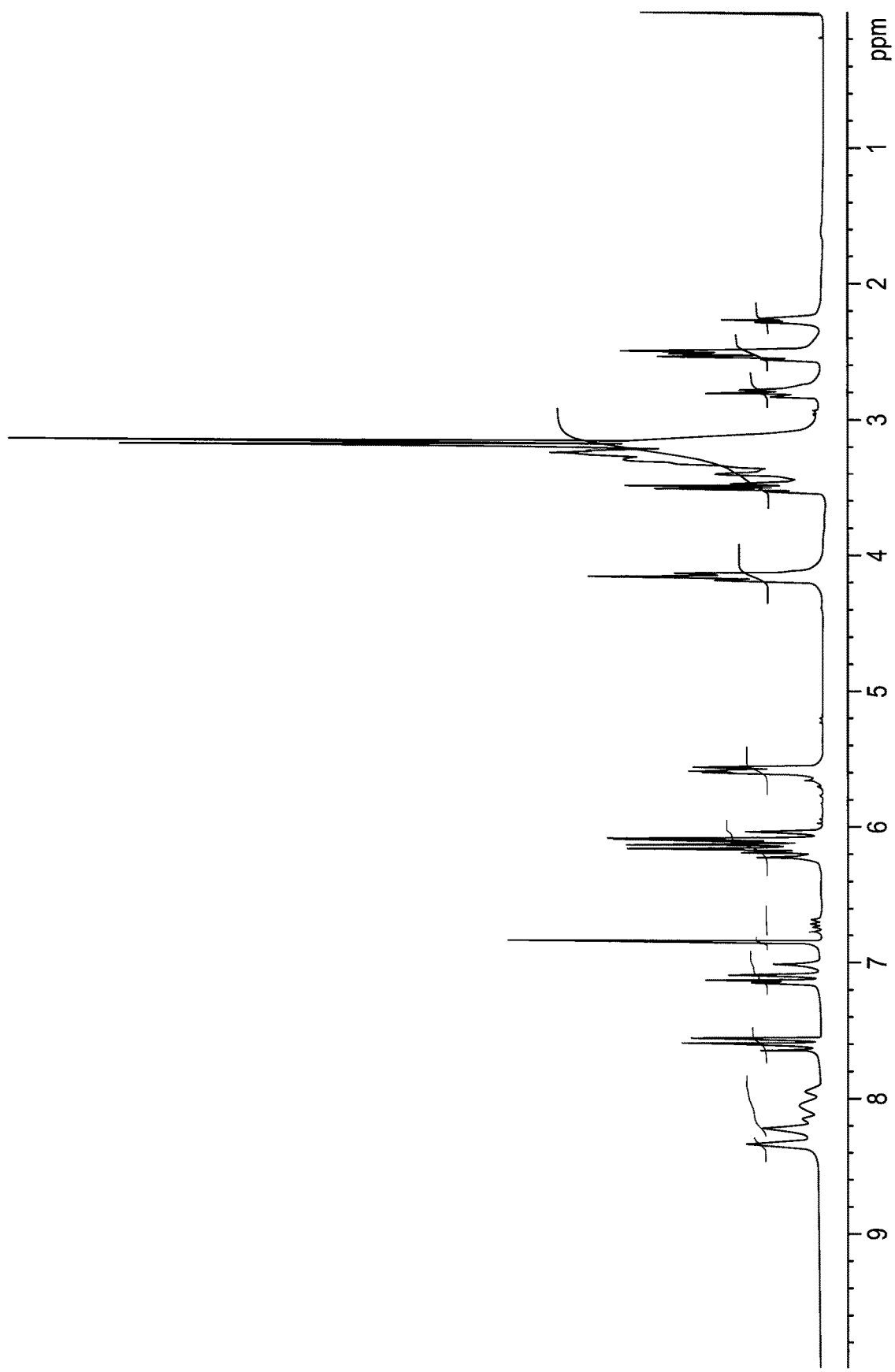
FIG. 4 depicts $^1$H NMR spectrum of hydrolytically stable imidazole-derived acrylamide precursor (XJ10-123).
Figure 5:
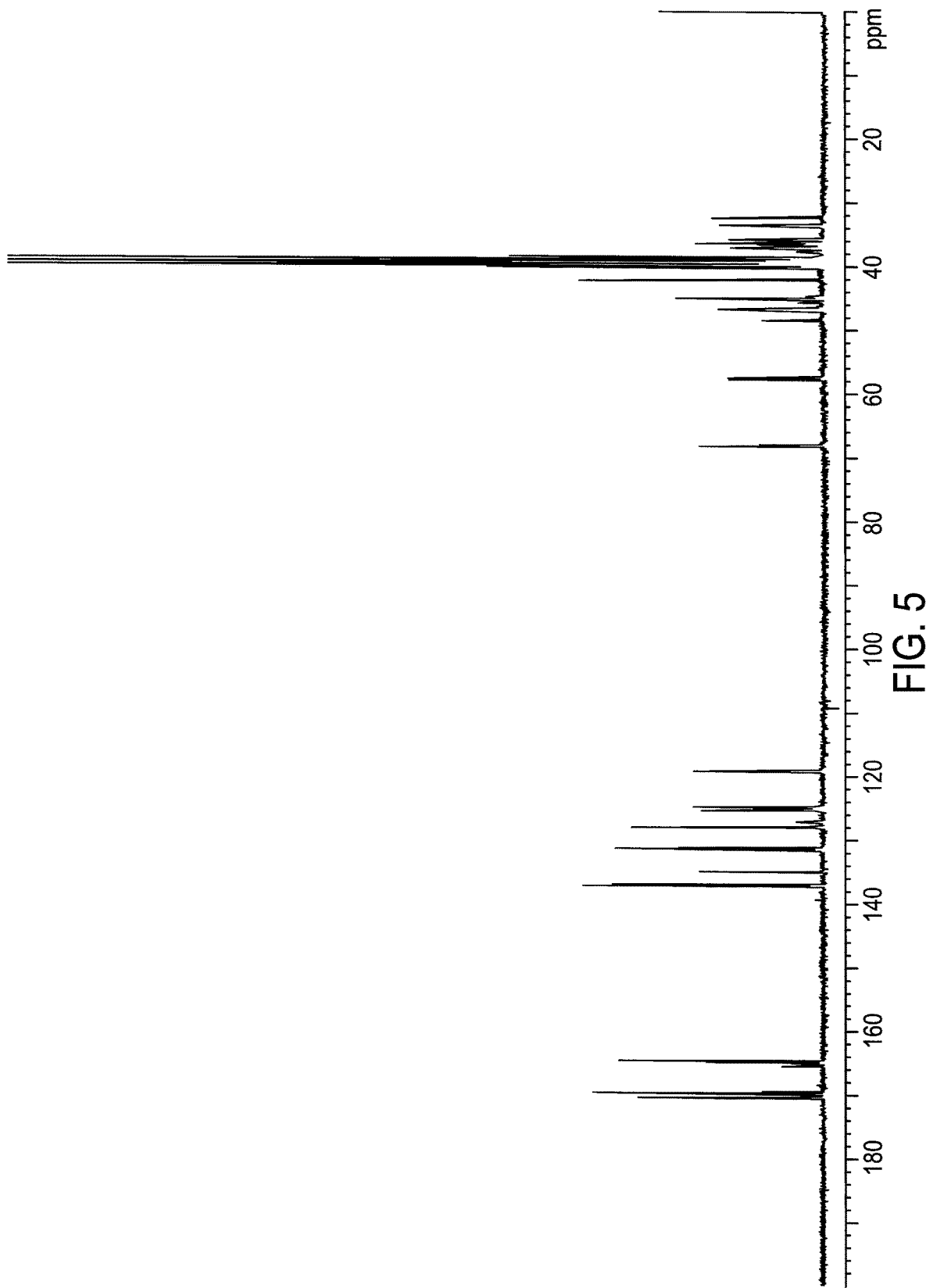
FIG. 5. depicts 13C NMR spectrum of hydrolytically stable imidazole-derived acrylamide precursor (XJ10-123).

Monoimidazole-bisacrylamide (XJ10-123/scheme-1) was prepared from unsymmetrical triacrylamide (FFM3) via a one-step solution process as described in the following:

Into a 500 ml three-neck round flask equipped with a mechanical agitator, 40.20 g (0.1515 mol) of an unsymmetrical trisacrylamide (FFM3, from Fujifilm) was charged. 180 g of methanol and 10.60 g of imidazole was then added to the flask. The reaction mixture was stirred until all the reactants were completely dissolved. The reaction was proceeded in oil-bath at room temperature for 19 h (as imidazole addition to acrylamide). 0.155 g of 1,8-Diazabicyclo [5.4.0]undec-7-ene (DBU) was added as catalyst. The reaction temperature was raised to 40-50° C. and kept for additional two weeks at 40-50° C. The reaction was monitored by NMR for it completion. After completion of reaction the product was purified with multiple extractions in methylene dichloride and with potassium carbonate aqueous solution to obtain XJ10-123. NMR confirmed structure of XJ10-123 (FIG. 4). The product was also characterized by C13 NMR (FIG. 5).

Synthetic Procedure for Hydrolytically Stable Imidazolium-Based Monomers (XJ10-118)

Hydrolytically stable antibacterial monomer (ABR-HS3, XJ10-118, scheme 3) was successfully prepared from the imidazole derivative of E-BPAD [monoimidazole-monoacrylamide, ABR-HS2, scheme-2)

Monoimidazole-monoacrylamide, ABR-HS2, could be readily prepared as following:

Unsymmetrical bisacrylamide, E-BPAD, was prepared from n-ethyl-propyl diamine and acryloyl chloride by MCA-T(as shown in scheme 4). NMR analysis confirmed its structure.

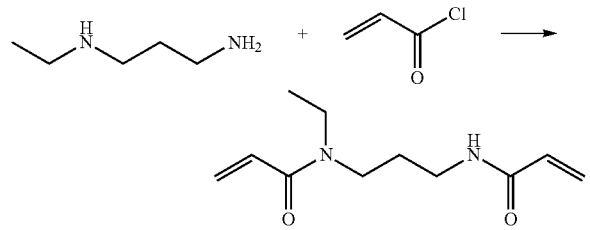

It was surprisingly discovered that highly selective Michael Addition could be readily achieved with dominant addition Michael donor toward the N-substituted acrylamide(s). Very little addition would occur towards the N-nonsubstituted acrylamide(s). For example, E-BPAD was reacted with imidazole to form monoimidazole-monoacrylamide as showed in Scheme 2, from which the mono-imidazolium-based monoacrylamide (ABR-HS3) (scheme 3) was prepared accordingly.

Figure 6:
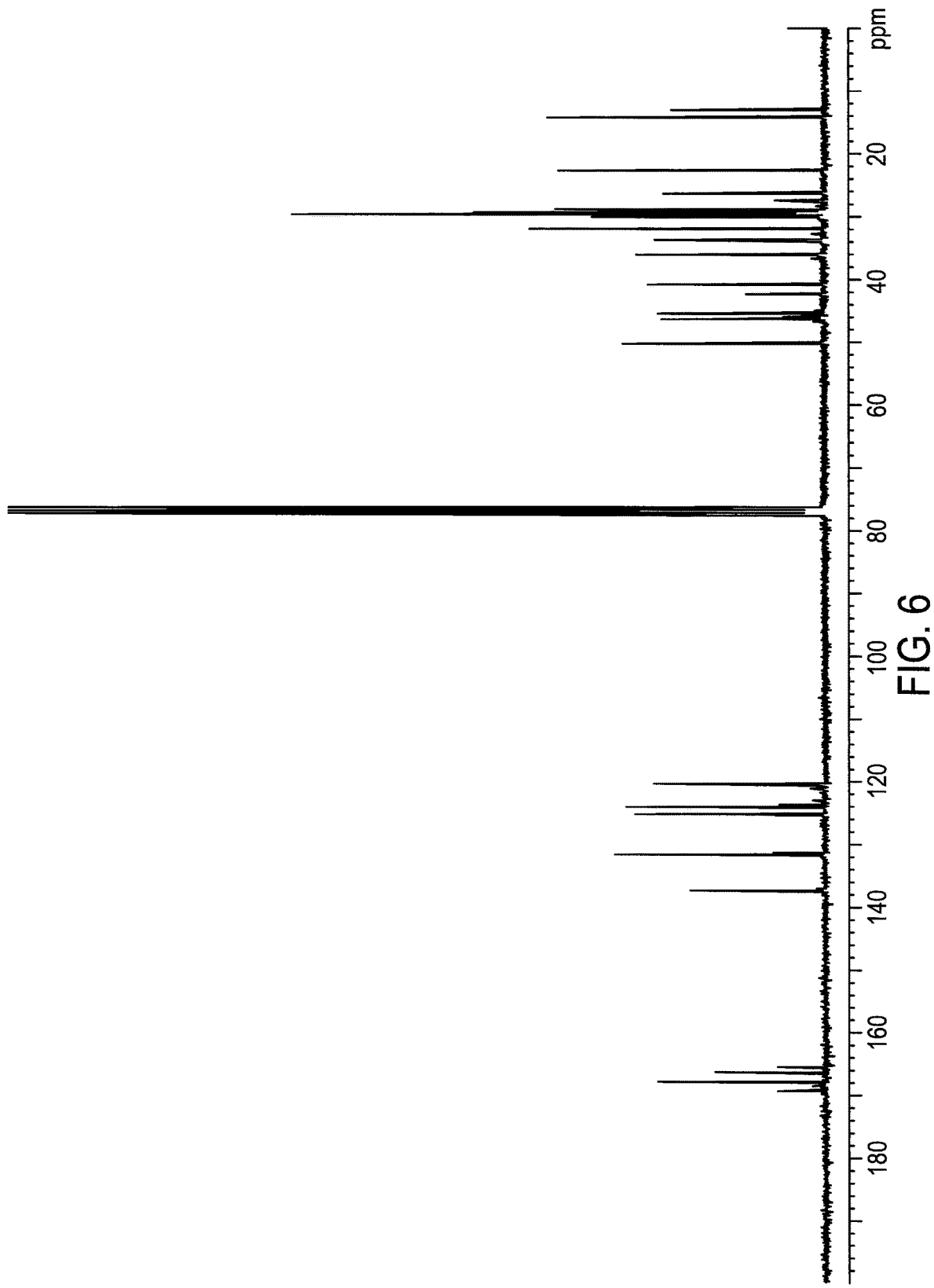
FIG. 6 depicts 13C NMR spectrum of hydrolytically stable C12B-imidazolium acrylamide (XJ10-118).
Figure 7:
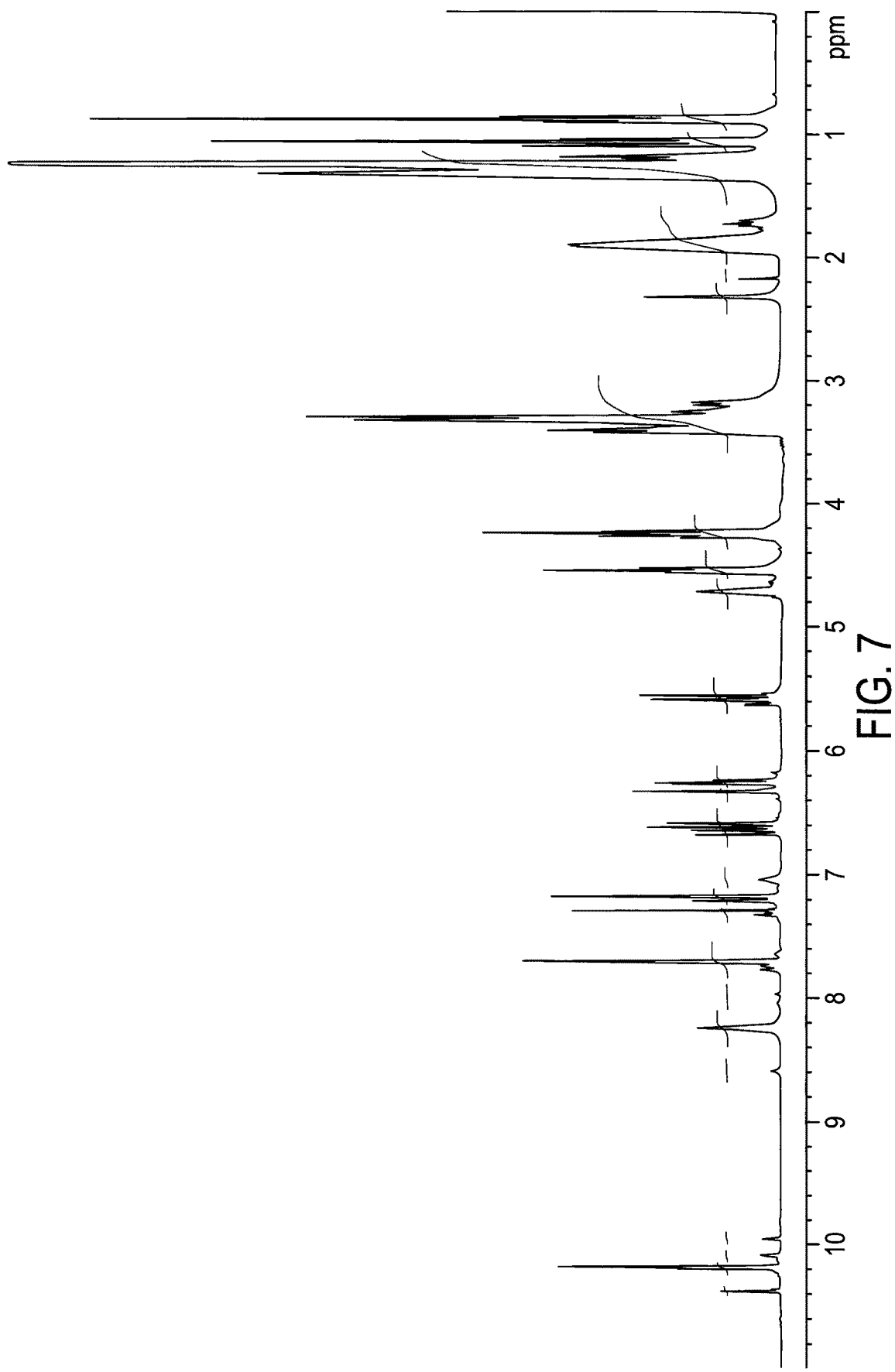
FIG. 7 depicts $^1$H NMR spectrum of hydrolytically stable C12B-imidazolium acrylamide (XJ10-118).

Into a 250 ml three-neck round flask equipped with a mechanical agitator 21.039 g (0.102 mol) of an unsymmetrical bisacrylamide (E-BPAD, from MCAT) was charged. 7.09 g of grounded imidazole was added to the flask. The reaction mixture was stirred until all the reactants were completely dissolved to a homogeneous liquid at room temperature. The reaction was proceeded in oil-bath at room temperature for 90 min (as imidazole addition to acrylamide). 0.094 g of 1,8-diazabicyclo [5,4,0]undec-7-ene (DBU) was added as catalyst. The reaction temperature was raised to 40-50° C. and kept for additional five weeks at 40-50° C. The reaction was monitored by NMR for it completion. 29.9 g of 1-bromododecane was added into the flask to proceed directly to the next step reaction at 40° C. for three days before it was stopped. The reaction was terminated by cooling down to room temperature and adding 100 g of hexane to the reaction mixture. The hexane solution part was decanted and acetone was added the residue. Crystals were formed from the solution. Crystal were filtered, dried and then recrystallized from acetone. NMR confirmed structure of XJ10-118 (FIG. 7) and HPLC confirmed its purity of 94%. 13C NMR also confirmed the structure of XJ10-118 (FIG. 6).

Microwave Reactor: Biotage Initiator plus was used for the synthesis of antibacterial nanogel with a variable resin compositions in 25 ml vial seal by capping with a Teflon septum fitted in an aluminum crimp top. The reaction temperature was set at 100° C., the reaction time was set for 5 min, 10 min or 15 min, respectively. The microwave absorption level was set as high for any ABR-C composition. The resulting solution was directly precipitated in 200 ml hexane. The nanogel was isolated by decanting the solvent. The isolated nanogel was re-dissolved in methylene dichloride and removed it via Rotavapor. Then final nanogel was further dried under vacuum for 8 h.

Batch Reaction (Conventional thermal Process): Solution copolymerizations of isobornyl methacrylate (IBMA) and urethane dimethacrylate (UDMA) (70/30 mole ratio) were conducted with 20% mol of mercaptoethanol (ME) and 20% mol of 1-dodecanethiol (DDT) as chain-transfer agent. Thermal-polymerizations used 1 wt % 2, 2-azobisisobutyronitrile at 75-80° C. in 2-butanone (MEK) or toluene, respectively. Methacrylate functionality could be reintroduced onto the nanoparticles by reaction with 2-isocyanatoethyl methacrylate (IEM) and thus reactive nanogels were resulted.

UDMA/POEMA is present as 30/70 (mole/mole) in the nanogel, AIBN as initiator and DDT as chain transfer agent are also added in the nanogel. (FIG. 1).

A variety of lab batches of nanogel based on UDMA/IBMA and/or UDMA/POEMA were successfully reproduced but lower yields of 50-70% consistently achieved, see examples in Table I and II. In addition, it was revealed that fractional macrogel could be formed along with the nanogel during the solvent removing process, though the initial precipitated nanogel could be dissolved completely. The presence of such a macrogel should negatively impact the yield and the dissolution of any resulting nanogel in a formulated resin mixture.

TABLE I

Effect of Resin Structure and Compositions on Copolymerization and Yield of Nanogels

| Nanogel (Process) | Core Resins g | | Transfer Agents g | | End Resin g | Final Weight g | | Yields % | |
|---|---|---|---|---|---|---|---|---|---|
| | UDMA | IBMA | 2ME | DDT | IEM | Actual | Calculated | w/IEM | w/o IEM |
| Example 1 (XJ9-29) (Conventional Thermal) | 24.06 | 26.06 | 2.77 | 6.70 | 5.36 | 38.5 | 64.95 59.59 | 59 | 65 |

TABLE I-continued

Effect of Resin Structure and Compositions on Copolymerization and Yield of Nanogels

| Nanogel (Process) | Core Resins g | | Transfer Agents g | | End Resin g | Final Weight g | | Yields % | |
|---|---|---|---|---|---|---|---|---|---|
|  | UDMA | IBMA | 2ME | DDT | IEM | Actual | Calculated | w/IEM | w/o IEM |
| Example 2 (XJ9-35) (Conventional Thermal) | 47.97 | 52.20 | 5.26 | 13.65 | 10.75 | 76.0 | 129.83 119.08 | 59 | 64 |
| Example 3 (XJ9-66) (Microwaved Thermal) | 2.40 | 2.62 | 0.33 | 0.66 | 0.57 | 4.40 | 6.58 6.01 | 67 | 73 |
| Example 4 (XJ9-67) (Microwaved Thermal) | 2.47 | 2.72 | 0.28 | 0.67 | 0.57 | 4.10 | 6.72 6.15 | 61 | 67 |
| Example 5 (XJ9-69) (Microwaved Thermal) | 2.44 | 2.64 | 0.29 | 0.67 | 0.56 | 4.53 | 6.60 6.04 | 69 | 75 |
| Example 6 (XJ9-73) w/XJ9-28 (Microwaved Thermal) | 3.56 | 2.64 | 0.27 | 0.66 | 0.57 | 4.20 | 7.77 7.20 | 54 | 58 |
| Example 7 (XJ9-76) w/XJ9-28 (Microwaved Thermal) | 3.54 | 2.70 | 0.26 | 0.68 | 0.54 | 4.00 | 7.72 7.18 | 52 | 56 |
| Example 8 (XJ9-77) w/XJ8-160 (Microwaved Thermal) | 2.41 | 5.85 | 0.27 | 0.68 | 0.54 | 9.0 | 9.75 9.21 | 92 | 98 |

TABLE II

Composition and Solvent Effect on Yield and Solubility of Nanogel via Batch Process

| Nanogel | Resin Composition | | | Reaction Condition | | | | | Solubility in Acetone |
|---|---|---|---|---|---|---|---|---|---|
|  | UDMA Mol % | IBMA Mol % | POEMA Mol % | Solvent Toluene(T) Methy ethyl ketone(MEK) | Temp. °C. | Time min | Conversion % | Yield % |  |
| 50 g Example 9 (XJ9-029) | Esstech 30 | Aldrich 70 | 0 | T | 80 | 55 | 84 | 70 | Not all |
| 100 g Example 10 (XJ9-033) | Esstech 30 | Aldrich 70 | 0 | T | 80 | 45 | 86 | 70 | Not all |
| 100 g Example 11 (XJ9-035) | Esstech 30 | Aldrich 70 | 0 | T | 80 | 35 | 71 | 70 | Not all |
| 100 g Example 12 (XJ9-086) | Esstech 30 | Aldrich 70 | 0 | T | 80 | 30 Quenched | 76 | 64 79 | Not all |
| 100 g Example 13 (XJ9-094) | Esstech 30 | TCI 70 | 0 | T | 80 | 30 | 76 | 70 | Not all |
| 100 g Example 14 (XJ10-44) | Aldrich 30 | TCI 70 | 0 | MEK | 80 | 70 | 81 | 55 | N/A |
| 100 g Example 15 (XJ9-112) | Esstech 28.8 | 0 | Aldrich 71.2 | T | 80 | 35 | 80 | N/A | macrogel |
| 100 g Example 16 (XJ9-114) | Esstech 30 | 0 | Aldrich 70 | T | 80 | 25 | 68 | 74 | Not all |

TABLE II-continued

Composition and Solvent Effect on Yield and Solubility of Nanogel via Batch Process

| | Resin Composition | | | Reaction Condition | | | | | |
|---|---|---|---|---|---|---|---|---|---|
| | | | | Solvent Toluene(T) | | | | | Solubility |
| Nanogel | UDMA Mol % | IBMA Mol % | POEMA Mol % | Methy ethyl ketone(MEK) | Temp. °C. | Time min | Conversion % | Yield % | in Acetone |
| 100 g Example 17 (XJ10-35) | Aldrich 25 | Aldrich 0 | 75 | MEK | 75 | 50 | 67 | 62 | Yes all |
| 100 g Example 18 (XJ10-38) | Aldrich 27.3 | 0 | Aldrich 72.7 | MEK | 80 | 55 | 82 | 73 | Yes all |

Thus effort was made to improve the yield of nanogel from such a process. More, particularly, nanogel based on UDMA/IBMA were prepared via microwave-assisted process, which allows rapid evaluation on the composition effect on the yield. For example, in comparison to the conventional reaction time of 60 min, reaction could be completed in 5-10 min in a microwave reactor and slightly higher yield could be achieved as well.

It was surprisingly noted that the highest yield of nanogel was achieved when the nanogel monomer is composed of an N-charged monomer, XJ8-160, as showed in Table I. Further, study did confirm the unique influence of such charged monomers, either as dimethacrylate to replace UDMA or as monomethacrylate to replace IBMA could lead to high yield, more than 90%, as showed in Table I, which was confirmed from an additional reaction (see Table III).

TABLE III

Composition and Solvent Effect on Yield and Solubility of Nanogel via MW Process

| | Resin Composition | | | | Solvent Toluene(T) | Reaction | | Solubility |
|---|---|---|---|---|---|---|---|---|
| Nanogel | UDMA Mol % | ABR-C Mol % | IBMA Mol % | POEMA Mol % | Methyl ethyl ketone (MEK) | Time Min. | Yield % | in Acetone |
| Example 19 (ZL1-003) | 30 | | 70 | | T | 5 | 48.6 | N |
| Example 20 (ZL1-005) | 20 | | 80 | | T | 5 | 33.7 | N |
| Example 21 (ZL1-007) | 40 | | 60 | | T | 5 | 61.1 | N |
| Example 22 (ZL1-011) | 20 | | 80 | | T | 5 | 34.7 | N |
| Example 23 (ZL1-017) | 30 | | 70 | | T | 5 | 51.3 | N |
| Example 24 (ZL1-085) | 30 | | 70 | | T | 5 | 56.0 | yes |
| Example 25 (ZL1-141) | 30 | | 70 | | T | 15 | 66.1 | yes |
| Example 26 (ZL1-143) | 30 | | 70 | | MEK | 15 | 51.1 | yes |
| Example 27 (ZL1-045) | 30 | | | 70 | T | 5 | 65.5 | yes |
| Example 28 (ZL1-053) | 30 | | | 70 | T | 5 | 69.5 | yes |
| Example 29 (ZL1-055) | 40 | | | 60 | T | 5 | 72.1 | yes |
| Example 30 (ZL1-031) | | 30 | 70 | | T | 5 | 65.3 | N |
| Example 21 (ZL1-033) | | 20 | 80 | | T | 5 | 51.0 | N |
| Example 32 (ZL1-037) | | 40 | 60 | | T | 5 | 62.1 | N |
| Example 33 (ZL1-067) | | 20 | | 80 | T | 5 | 58.7 | yes |
| Example 34 (ZL1-071) | | 30 | | 70 | T | 5 | 55.1 | yes |
| Example 35 (ZL1-073) | | 40 | | 60 | T | 5 | 60.3 | yes |
| Example 36 (ZL1-077) | | 30 | | 70 | T | 5 | 56.1 | Yes/hazy |
| Example 37 (ZL1-095) | | 30 | | 70 | MEK | 5 | 68.5 | yes |
| Example 38 (ZL1-101) | | 30 | | 70 | MEK | 10 | 72.8 | yes |

TABLE III-continued

Composition and Solvent Effect on Yield and Solubility of Nanogel via MW Process

| Nanogel | Resin Composition | | | | Solvent Toluene(T) Methyl ethyl ketone (MEK) | Reaction Time Min. | Yield % | Solubility in Acetone |
|---|---|---|---|---|---|---|---|---|
| | UDMA Mol % | ABR-C Mol % | IBMA Mol % | POEMA Mol % | | | | |
| Example 39 (ZL1-103) | | 30 | | 70 | MEK | 15 | 76.4 | yes |
| Example 40 (ZL1-111) | | 30 | | 70 | MEK | 15 | 94.5 | yes |
| Example 41 (ZL1-147) | | 30 | | 70 | MEK | 15 | 76.1 | yes |
| Example 42 (ZL1-151) | | 30 | | 70 | MEK | 15 | 95.0 | yes |
| Example 43 (ZL1-115) | | 30 | 70 | | MEK | 5 | 57.7 | yes |
| Example 44 (ZL1-117) | | 30 | 70 | | MEK | 10 | 61.2 | yes |
| Example 45 (ZL1-119) | | 30 | 70 | | MEK | 15 | 61.9 | yes |

Further, it was another objective of this study to explore the feasibility in making antibacterial nanogel by incorporating newly developed polymerizable antibacterial resins, ABR-C into nanogel. Therefore, a variety of nanogels were prepared via microwave process (as shown in Table III) including UDMA/IBMA (see Example 19, Example 21, Example 22, Example 23 and Example 24); UDMA/POEMA (see Example 27, Example 28 and Example 29); ABR-C/IBMA (see Example 43, Example 44, and Example 45); ABR-C/POEMA (see Example 33, Example 35, Example 36, Example 37, Example 38, Example 39 and Example 40).

By switching the monomethacrylate IBMA with POEMA, higher yield could be readily resulted. In addition, when switching the dimethacrylate UDMA by ABR-C, the antibacterial dimethacrylate resin, higher yield would result especially when it is copolymerized with POEMA. As demonstrated by the examples in Table III, ABR-C/POEMA (30/70) in MEK would offer higher yield of 68-95% in comparison of 58-62% for ABR-C/IBMA in MEK and 51-65% for ABR-C/IBMA in toluene, respectively.

Antibacterial nanogel based on ABR-C and other comonomer resins were synthesized in a microwave reactor by copolymerizing ABR-C and POEMA or IBMA. Improved yields of 68-95% were achieved for ABR-C/POEMA (30/70, Example 40) or ABR-C/IBMA (30/70, Example 30) vs UDMA/IBMA (30/70, Example 25 and Example 26) in 51-66%. In addition the improved solubility of such nanogel system was achieved in MEK rather than toluene, which was critical for its redispersability of such nanogel in resin matrix.

Meanwhile as the improvement in yield was achieved via incorporating such N-charged monomers, a new class of nanogels that are composed of different polymerizable imidazolium resins, dimethacrylate (XJ9-28) and monomethacrylate (XJ8-160) were successfully prepared via microwave process. Distinguished rheological property was demonstrated by the two "charged" nanogels.

TABLE IV

Resin Compositions of New Charged Nanogels

| Resin Compositions | Jeff's Nanogel Example 5 grams (mmol) | Antibacterial Nanogel 1 Example 7 grams (mmol) | Antibacterial Nanogel 2 Example 8 grams (mmol) |
|---|---|---|---|
| Dimethacrylate Resin | | | |
| UDMA | 2.40 (5.10) | 0 | 2.40 (5.10) |
| Antibacterial Resin (XJ9-28) | 0 | 3.51 (5.10) | 0 |
| Monomethacrylate Resin | | | |
| IBMA | 2.60 (11.69) | 2.60 (11.69) | 0 |
| Antibacterial Resin (XJ8-160) | 0 | 0 | 5.86 (11.69) |
| Chain Transfer Agents/Initiator | | | |
| ME | 0.26 (20% mol) | 0.26 (20% mol) | 0.26 (20% mol) |
| DDT | 0.68 (20% mol) | 0.68 (20% mol) | 0.68 (20% mol) |
| AIBN | 0.05 (1% wt) | 0.05 (1% wt) | 0.05 (1% wt) |

Nanogel/ZL1-077 (Example 36 from toluene solution) and Nanogel/ZL1-111 (Example 40 from MEK) were formulated with conventional TPH resin (Example 46 vs Composite Example 3) and then they were formulated into composite pastes (Composite Example 1, Composite Example 2, Composite Example 3 and Composite Example 4, respectively, with different filler loading of 55%-70% (see Table VII and VIII). The antibacterial activity against *S. aureus* were tested as showed in FIG. 2 and FIG. 3. Obviously both Composite Example 1 and 2, and Composite Example 3 and 4 could demonstrate strong antibacterial activity in comparison to the control neutral composite.

TABLE V

Compositions of Formulated Resins with Antibacterial Nanogel

| Formulated Resin Compositions | Example 46 (ZL1-089) | |
|---|---|---|
| | wt | % |
| Example 36 (ZL1-077) | 9.0 | 13.85 |
| TPH Resin/999446 | 65.0 | 86.15 |
| CQ | 0.0148 | 0.165 |
| EDAB | 0.027 | 0.300 |
| BHT | 0 | 0.025 |

Furthermore, the new antibacterial composites, Composite Example 1 and 2, were formulated with 72% and 55% of filler respectively, from such antibacterial nanogel (Example 36). It was noted Example 36 got limited solubility in TPH resin. Even at 13.85% wt/wt loading level for Example 36, longer mixing time was needed and an immediate composite compounding process was made to avoid further phase separation of such antibacterial nanogel from the TPH resin matrix. A moderate mechanical property was resulted but highly effective antibacterial activity was confirmed by the 24 h contact test, in which >99.9997% of *S. aureus* was killed. Surprisingly the Composite Example 2 appears less effective in killing *S aureus* that Composite Example 1, which should be attributed the inconsistent dispersion of Example 36 in TPH resin due to its limited solubility. Therefore, similar composites, Composite Example 3 and Composite Example 4 were formulated from same batch of activated resin Example 47 by using the ABR-C/POEMA (30/70) nanogel prepared in MEK (Example 40). Indeed as demonstrated by the antibacterial activity test, consistent and highly effective antibacterial effectiveness were resulted, >99.99989% of *S. aureus* was killed.

TABLE VI

Compositions and Properties of Formulated Composite with Antibacterial Nanogel

| Composite Compositions | Composite Example 1 (ZL1-90) | Composite Example 2 (ZL1-99) |
|---|---|---|
| Resin Blend | Example 46 (ZL1-089) 28.00% | Example 46 (ZL1-089) 45.00% |
| Filler Blend | BABG/999117, 65.8% EG-9726/907645, 32.9% Can-O-Sil TS720/431350, 1.3% 72.00% | BABG/999117, 65.8% EG-9726/907645, 32.9% Can-O-Sil TS720/431350, 1.3% 55.00% |
| Stress @ 60 min (QHLBlue) MPa | 2.76 | 2.67 |
| Compr. St. (MPa) | 246 ± 17 | 220 ± 9 |
| Compr. Mod. (MPa) | 4240 ± 260 | 3240 + 120 |
| Flex. St. (MPa) | 90 ± 5 | 85 ± 6 |
| Flex. Mod. (MPa | 5780 ± 310 | 4000 ± 200 |

TABLE VII

Compositions of Formulated Resins with Antibacterial Nanogel

| Resin Compositions | Example 47 (ZL1-125A and ZL1-125B) | |
|---|---|---|
| | wt | % |
| Example 40 (ZL1-111) | 9.41 | 14.37 |
| TPH Resin/999446 | 65.09 | 85.63 |
| CQ (extra) | 0.0158 | 0.15 |
| EDAB (extra) | 0.0272 | 0.300 |
| BHT (extra) | 0 | 0.025 |

TABLE VIII

Compositions and Properties of Formulated Composite with Antibacterial Nanogel

| Composite Compositions | Composite Example 3 (ZL1-125) | Composite Example 4 (ZL1-137) |
|---|---|---|
| Resin Blend | Example 46 (ZL1-125A) 28.00% | Example 46 (ZL1-125B) 28.00% |
| Filler Blend | BABG/999117, 65.8% EG-9726/907645, 32.9% Can-O-Sil TS720/431350, 1.3% 70.89% | BABG/999117, 67.1% EG-9726/907645, 32.9% 70.80% |

TABLE VIII-continued

Compositions and Properties of Formulated Composite with Antibacterial Nanogel

| Composite Compositions | Composite Example 3 (ZL1-125) | Composite Example 4 (ZL1-137) |
|---|---|---|
| Compr. St. (MPa) | 213 ± 14 | 212 ± 12 |
| Compr. Mod. (MPa) | 3899 ± 400 | 3846 ± 460 |
| Flex. St. (MPa) | 83 ± 5 | 95 ± 9 |
| Flex. Mod. (MPa | 5666 ± 300 | 5835 ± 210 |

Though moderate mechanical properties were resulted due to increased water absorption, highly effective antibacterial activity was clearly demonstrated by the 24 h contact test, in which >99.9997% of *S. aureus* was killed for Composite Example 1 and Composite Example 2. More importantly, the improved solubility of such nanogel prepared in MEK led to good dispersion in resin matrix as evident by the consistent and highly effective antibacterial effectiveness were resulted, >99.99989% of *S. aureus* was killed for Composite Example 3 and Composite Example 4.

While the present disclosure has been described with reference to one or more embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims. In addition, all numerical values identified in the detailed description shall be interpreted as though the precise and approximate values are both expressly identified.

The invention claimed is:

1. A polymerizable antibacterial nanogel derived from a monomer mixture comprising:
   (a) a polymerizable antibacterial monomer having a compound of Formula I

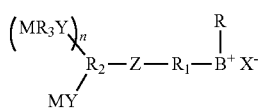

Formula I wherein
   M is vinylether, vinylester, vinylamine, allyl, acrylamide, methacrylamide, acrylate, or methacrylate moiety;
   Y and Z are an independently a same or different alkylene, oxyalkylene, aminoalkylene or thioalkylene having from 1 to 4 carbons, arylene, carbonate, carboxylate, ester group, amide or a direct bond;
   $R_1$ is a divalent hydrocarbon radical having from 2 to 18 carbons;
   $R_2$ and $R_3$ are an independently a same or different straight or branched chain alkylene having from 1 to 4 carbons or a direct bond;
   B is an imidazolium, pyridinium, ammonium or sulfonium group;
   R is a linear or branched alkyl having from 4 to 16 carbon atoms or a direct bond;
   X is a counter ion moiety; and
   n is an integer of from 0 to 4,
   (b) at least one polymerizable resin monomer having at least one (meth)acrylate or (meth)acrylamide group,
   (c) at least one chain transfer agent in a concentration of from 25 to 35% mole/mole of the total ethylenically unsaturated group in the monomer mixture, and
   (d) an initiator;
   wherein the polymerizable antibacterial nano el is essentially free of macrogel.

2. The polymerizable antibacterial nanogel according to claim 1, wherein the polymerizable antibacterial monomer comprises a compound of Formula II:

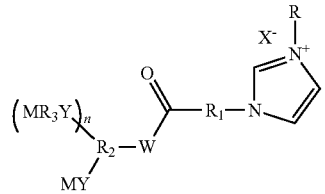

Formula II wherein,
M is vinylether, vinylester, vinylamine, allyl, acrylamide, methacrylamide, acrylate, or methacrylate moiety;
Y is an alkylene, oxyalkylene or thioalkylene having from 1 to 4 carbons, carbonate, carboxylate, ester group, or direct bond;
W is O, $NR_4$ or a direct bond;
$R_1$ is a divalent hydrocarbon radical having from 2 to 18 carbons;
$R_2$ and $R_3$ are an independently a same or different straight or branched chain alkylene having from 1 to 4 carbons;
$R_4$ is an alkyl having from 1 to 4 carbons or $R_2M$;
R is a linear or branched alkyl having from 4 to 16 carbon atoms;
X is a counter ion moiety; and
n is an integer of from 0 to 1.

3. The polymerizable antibacterial nanogel according to claim 1, wherein the polymerizable resin monomer having at least one (meth)acrylate or methacrylamide group is selected from the group consisting of mono-, di-, tri- and tetra functional monomer.

4. The polymerizable antibacterial nanogel according to claim 1, wherein the polymerizable resin monomer is selected from the group consisting of 2,2'-bis [4-(3-methacryloxy-2-hydroxy propoxy)-phenyl] propane (bis-GMA), tetraethyleneglycoldi(meth)acrylate (TEGDMA), urethane dimethacrylate (UDMA), trimethylolpropane trimethacrylate, $C_1$-$C_{20}$ alkyl(meth)acrylates, an aromatic methacrylate, a hydroxy alkyl (meth)acrylate, and a (meth)acrylamide.

5. The polymerizable antibacterial nanogel according to claim 2, wherein n is 1.

6. The polymerizable antibacterial nanogel according to claim 5, wherein the polymerizable antibacterial monomer is present in a range of from 5 to 45 mole percent based on total moles of the monomer mixture.

7. The polymerizable antibacterial nanogel according to claim 2, wherein n is 0.

8. The polymerizable antibacterial nanogel according to claim 7, wherein the polymerizable antibacterial monomer is present in a range of from 5 to 95 mole percent based on total moles of the monomer mixture.

9. The polymerizable antibacterial nanogel according to claim 1, wherein the at least one ethylenically unsaturated group of the polymerizable antibacterial monomer is a methacrylate group and the at least one (meth)acrylate group of polymerizable resin monomer is a methacrylate group such that a combination of the methacrylate group of the polymerizable antibacterial monomer and the methacrylate group of the polymerizable resin monomer is present in a range of from 50 to 90 mole percent based on total moles of the monomer mixture.

10. The polymerizable antibacterial nanogel according to claim 9, wherein the polymerizable resin monomer is the $C_1$-$C_{20}$ alkyl(meth)acrylate.

11. The polymerizable antibacterial nanogel according to claim 9, wherein the polymerizable resin monomer is an aromatic methacrylate.

12. The polymerizable antibacterial nanogel according to 10, wherein the polymerizable resin monomer is hydroxyl alkyl acrylate, hydroxyl alkyl methacrylate, hydroxyl alkyl acrylamide, or hydroxyl alkyl (meth)acrylamide.

13. The polymerizable antibacterial nanogel according to claim 1, wherein said chain transfer agent is 1-dodecanethiol.

14. The polymerizable antibacterial nanogel according to claim 1, wherein said initiator is azobisisobutyronitrile.

15. The polymerizable antibacterial nanogel according to claim 1, wherein said initiator is present in a concentration of from 0.5 to 2.0 wt/wt of total ethylenically unsaturated group in the monomer mixture.

16. The polymerizable antibacterial nanogel according to claim 2, wherein polymerizable antibacterial monomer comprises an amide of Formula III

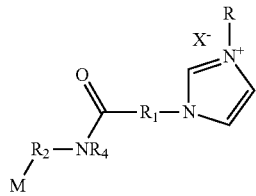

wherein
M is allyl, acrylamide, or methacrylamide moiety;
$R_1$ is a divalent hydrocarbon radical having from 2 to 18 carbons;
$R_2$ is an independently a same or different straight or branched chain alkylene having from 1 to 4 carbons;
$R_4$ is an alkyl having from 1 to 4 carbons or $R_2M$;
R is a linear or branched alkyl having from 4 to 16 carbon atoms; and
X is a counter ion moiety.

17. The polymerizable antibacterial nanogel according to claim 16, wherein the polymerizable antibacterial nanogel is hydrolytically stable and water soluble.

18. A method of forming a hydrolytically stable, water soluble polymerizable monomer containing asymmetric polyacrylamides, the method comprising:
(a) reacting the asymmetric polyacrylamides in the presence of a Michael donor under conditions selected to yield mono-substituted asymmetric polyacrylamide;
wherein the Michael donor is imidazole; and
(b) converting the imidazole of mono-substituted asymmetric polyacrylamide monomer to an imidazolium.

19. The method of claim 18, wherein the step of converting the imidazole of mono-substituted
asymmetric polyacrylamide monomer to an imidazolium comprises reacting mono-substituted asymmetric polyacrylamide monomer with RX;
wherein
R is a linear or branched alkyl having from 4 to 16 carbon atoms; and
X is a counter ion moiety.

20. A method of forming a hydrolytically stable, water soluble polymerizable antibacterial
monomer containing asymmetric polyacrylamides of Formula III

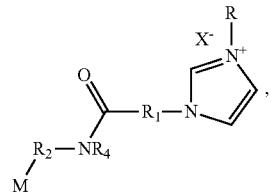

said method comprising steps of:
reacting an asymmetric polyacrylamides of formula

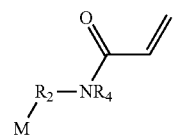

in the presence of a Michael donor under conditions selected to yield mono-substituted asymmetric polyacrylamide of formula

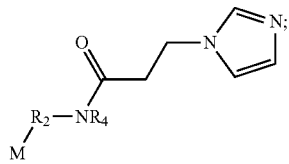

wherein the Michael donor is imidazole;
(b) converting the imidazole of mono-substituted asymmetric polyacrylamide monomer to an imidazolium by reacting mono-substituted asymmetric polyacrylamide monomer with RX to yield hydrolytically stable, water soluble polymerizable antibacterial monomer containing asymmetric polyacrylamides of Formula III

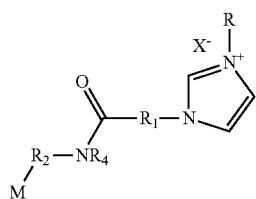

wherein

M is allyl, acrylamide, or methacrylamide moiety;

$R_1$ is a divalent hydrocarbon radical having from 2 to 18 carbons;

$R_2$ is an independently a same or different straight or branched chain alkylene having from 1 to 4 carbons;

$R_4$ is an alkyl having from 1 to 4 carbons or $R_2M$,

R is a linear or branched alkyl having from 4 to 16 carbon atoms; and

X is a counter ion moiety.

21. A method of preparing a polymerizable antibacterial nanogel, the method comprising:

(a) combining (i) a polymerizable antibacterial monomer having a compound of Formula I

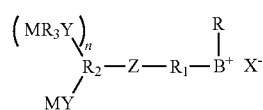 Formula I wherein,

M is vinylether, vinylester, vinylamine, allyl, acrylamide, methacrylamide, acrylate, or methacrylate moiety;

Y and Z are an independently a same or different alkylene, oxyalkylene, aminoalkylene or thioalkylene having from 1 to 4 carbons, arylene, carbonate, carboxylate, ester group, amide or a direct bond;

$R_1$ is a divalent hydrocarbon radical having from 2 to 18 carbons;

$R_2$ and $R_3$ are an independently a same or different straight or branched chain alkylene having from 1 to 4 carbons or a direct bond;

B is an imidazolium, pyridinium, ammonium or sulfonium group;

R is a linear or branched alkyl having from 4 to 16 carbon atoms or a direct bond;

X is a counter ion moiety; and n is an integer of from 0 to 4, (ii) at least one polymerizable resin monomer having at least one (meth)acrylate or (meth)acrylamide group, (iii) at least one chain transfer agent in a concentration of from 25 to 35% mole/mole of the total ethylenically unsaturated group in the monomer mixture, and (iv) an initiator, in presence of a solvent in a microwave reactor, (b) initiating a polymerization reaction, and (c) recovering the polymerizable antibacterial nanogel from the solvent after polymerization;

wherein the polymerizable antibacterial nanogel is essentially free of macrogel.

22. The method according to claim 21, wherein the solvent is methyl ethyl ketone or toluene.

23. The method according to claim 22, wherein the solvent is methyl ethyl ketone.

24. An antibacterial dental composite comprising an antibacterial nanogel modified resin matrix, and filler particles; wherein the antibacterial nanogel modified resin matrix comprises a polymerizable antibacterial nanogel, a polymerizable resin, an initiator and a stabilizer, and wherein the polymerizable antibacterial nanogel is obtained from a mixture comprising: (i) a polymerizable antibacterial monomer having a compound of Formula I

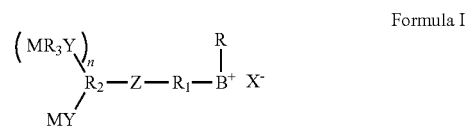 Formula I wherein,

M is vinylether, vinylester, vinylamine, allyl, acrylamide, methacrylamide, acrylate, or methacrylate moiety;

Y and Z are an independently a same or different alkylene, oxyalkylene, aminoalkylene or thioalkylene having from 1 to 4 carbons, arylene, carbonate, carboxylate, ester group, amide or a direct bond;

$R_1$ is a divalent hydrocarbon radical having from 2 to 18 carbons;

$R_2$ and $R_3$ are an independently a same or different straight or branched chain alkylene having from 1 to 4 carbons or a direct bond;

B is an imidazolium, pyridinium, ammonium or sulfonium group;

R is a linear or branched alkyl having from 4 to 16 carbon atoms or a direct bond;

X is a counter ion moiety; and n is an integer of from 0 to 4 (ii) a polymerizable resin monomer having at least one (meth)acrylate or (meth)acrylamide group, (iii) at least one chain transfer agent in a concentration of from 25 to 35% mole/mole of the total ethylenically unsaturated group in the monomer mixture, and (iv) an initiator; wherein the polymerizable antibacterial nanogel is essentially free of macrogel.

25. The antibacterial dental composite according to claim 24, wherein the antibacterial nanogel modified resin matrix is present in the composite in a concentration of from 20 to 50 weight percent based on a total weight of the composite.

26. The antibacterial dental composite according to claim 24, wherein the filler particles are present in the composite in a concentration of from 30 to 90 weight percent based on a total weight of the composite.

27. The antibacterial composite according to claim 24, wherein the composite demonstrates antibacterial activity against *S. aureus*.

28. The antibacterial dental composite according to claim 24, wherein the polymerizable antibacterial nanogel is present in the antibacterial nanogel modified resin matrix in a concentration of from 3.0 to 10.0 weight percent based on a total weight of the antibacterial nanogel modified resin matrix.

* * * * *